(12) United States Patent
Chaikin et al.

(10) Patent No.: US 9,206,471 B2
(45) Date of Patent: Dec. 8, 2015

(54) SELF-REPLICATING MATERIALS

(75) Inventors: Paul Michael Chaikin, Pennington, NJ (US); David Pine, New York, NY (US); Nadrian C. Seeman, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 932 days.

(21) Appl. No.: 12/482,823

(22) Filed: Jun. 11, 2009

(65) Prior Publication Data

US 2010/0090180 A1 Apr. 15, 2010

Related U.S. Application Data

(63) Continuation-in-part of application No. PCT/US2007/025749, filed on Dec. 17, 2007.

(60) Provisional application No. 61/182,597, filed on May 29, 2009, provisional application No. 60/875,272, filed on Dec. 15, 2006.

(51) Int. Cl.
| | |
|---|---|
| G02F 1/361 | (2006.01) |
| C09K 3/00 | (2006.01) |
| C12Q 1/68 | (2006.01) |
| B82Y 5/00 | (2011.01) |
| B82Y 20/00 | (2011.01) |
| C12N 15/10 | (2006.01) |

(52) U.S. Cl.
CPC . *C12Q 1/682* (2013.01); *B82Y 5/00* (2013.01); *B82Y 20/00* (2013.01); *C12N 15/10* (2013.01); *C12N 15/1031* (2013.01); *C12N 15/1068* (2013.01)

(58) Field of Classification Search
USPC .......................................... 252/582, 183.11
See application file for complete search history.

(56) References Cited

U.S. PATENT DOCUMENTS

| | | | |
|---|---|---|---|
| 5,989,813 | A | 11/1999 | Gerdes |
| 2005/0037397 | A1 | 2/2005 | Mirkin et al. |
| 2006/0040286 | A1 | 2/2006 | Mirkin et al. |

FOREIGN PATENT DOCUMENTS

WO    WO 98/04740    2/1998

OTHER PUBLICATIONS

Marie-Pierre Valignat, Olivier Theodoly, John C. Crocker, William B. Russel, and Paul M. Chaikin, Reversible self-assembly and directed assembly of DNA-linked micrometer-sized colloids, PNAS, Mar. 22, 2005, vol. 102, No. 12, 4225-4229.*
Understanding DNA, The molecule & How it works by Chris R. Calladine, Horace R. Drew, Ben F. Luisi, Andrew A. Travers, Thrid Edition, 2004, Copyright © 2004, Elsevier Ltd. All rights reserved.*
Seeman et al., "Nucleic Acid Nanostructures: Bottom-Up Control of Geometry on the Nanoscale," *Rep. Prog. Phys.*, vol. 68 (2005) pp. 237-270.
Valignat et al., "Reversible Self-Assembly and Directed Assembly of DNA-linked Micrometer-Sized Colloids", *PNAS*, Mar. 22, 2005, vol. 102, No. 12, pp. 4225-4229.

\* cited by examiner

*Primary Examiner* — Robert M Kelly
(74) *Attorney, Agent, or Firm* — Foley & Lardner LLP

(57) ABSTRACT

The invention provides micron and sub-micron scale particles designed to recognize and selectively interact with each other by exploiting the recognition and specificity enabled by DNA-sequence-encoded coatings. Such materials possess sufficient information coded in their chemical and physical interactions to self assemble and self replicate. The invention further provides methods of using such materials to create self replicating and organizing materials. Replicated copies are permanently linked and then thermally detached, freeing them to act as templates for further growth. This new class of condensed matter systems, provides means to design and control the structure and function of materials and machines from the microscopic to life-size. In another aspect of the invention, depletion type forces and depletion zones can be utilized in the implementation of the self assembly and self replication of materials, including without limitation colloidal particles. The invention further provides novel means of synthesis and materials built by such synthesis, which may be used in a variety of applications, including microelectronics.

10 Claims, 39 Drawing Sheets

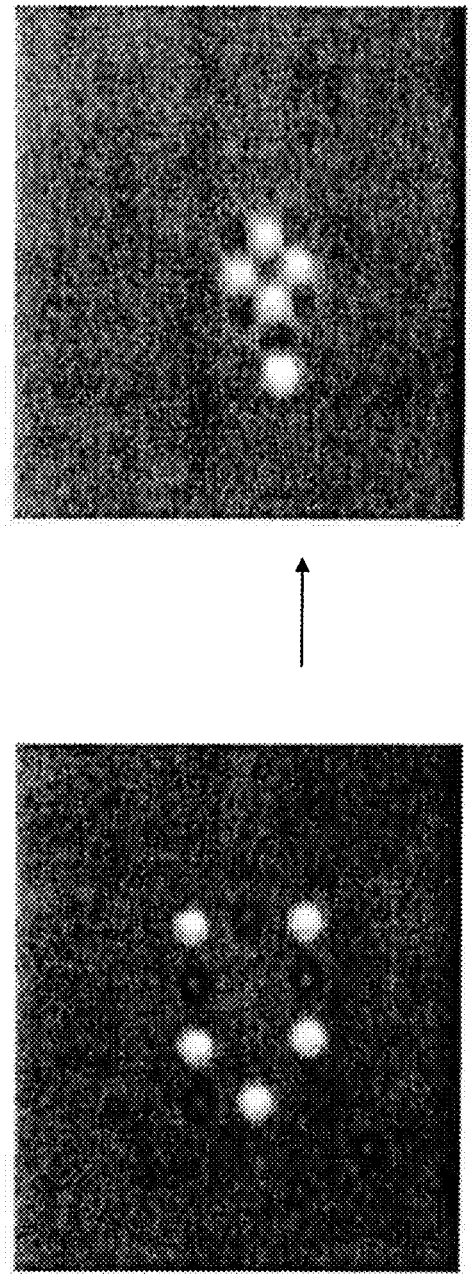

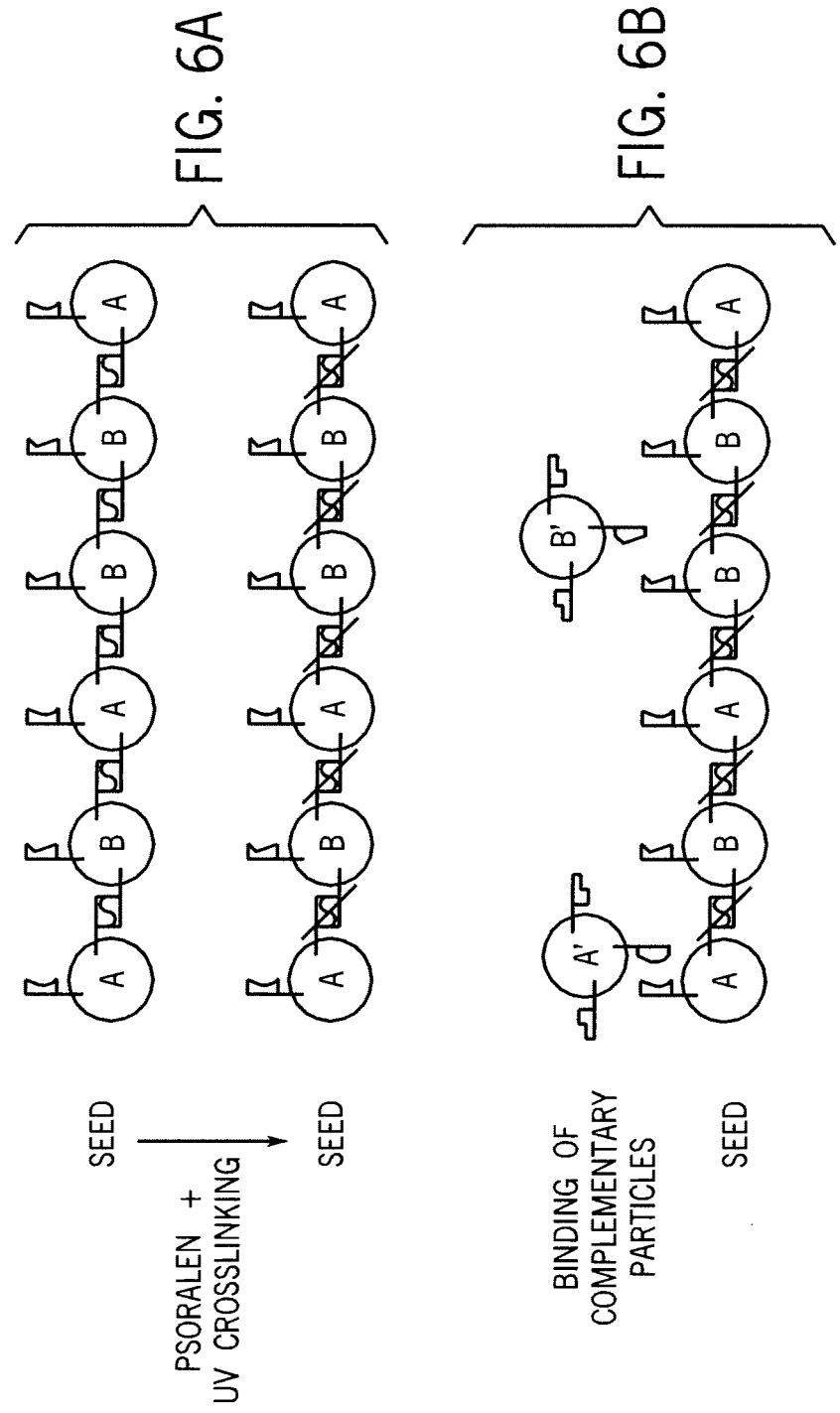

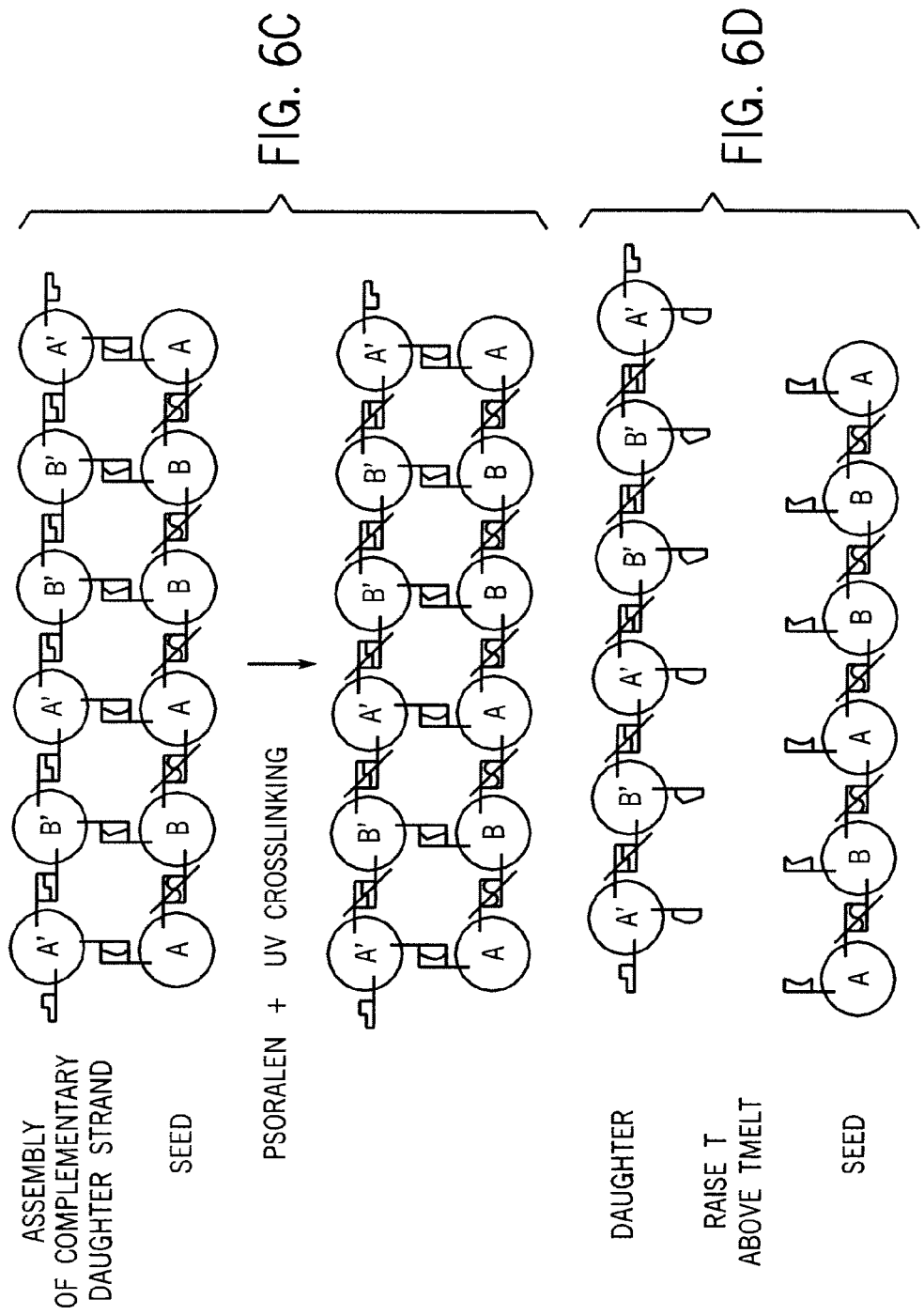

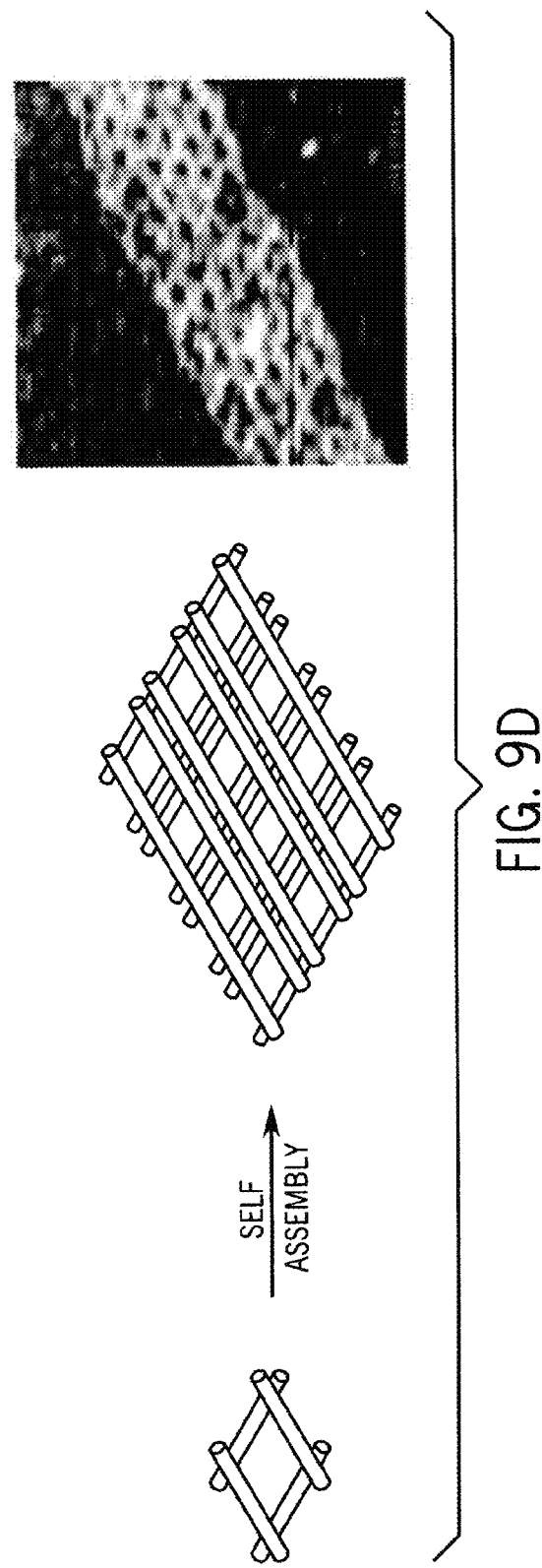

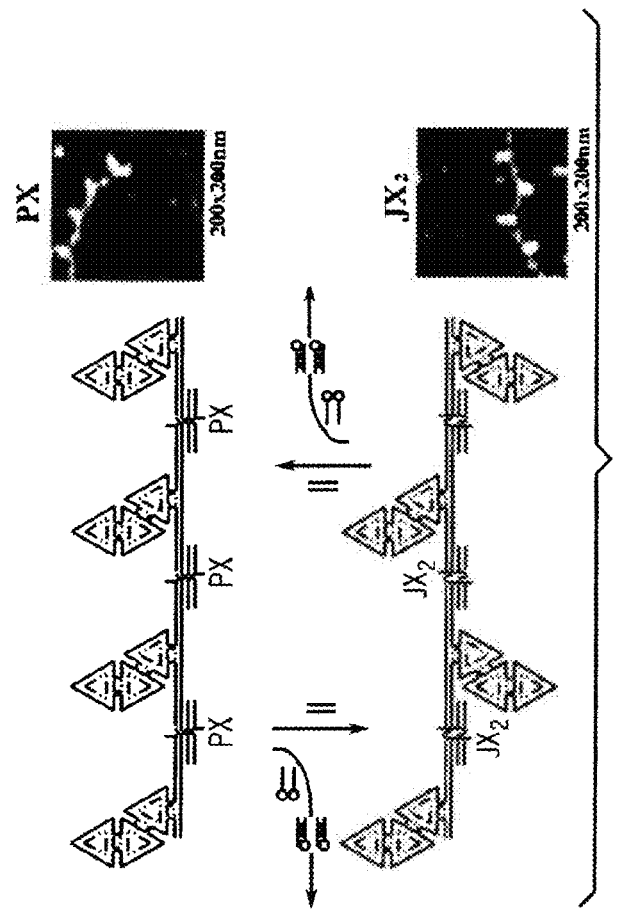
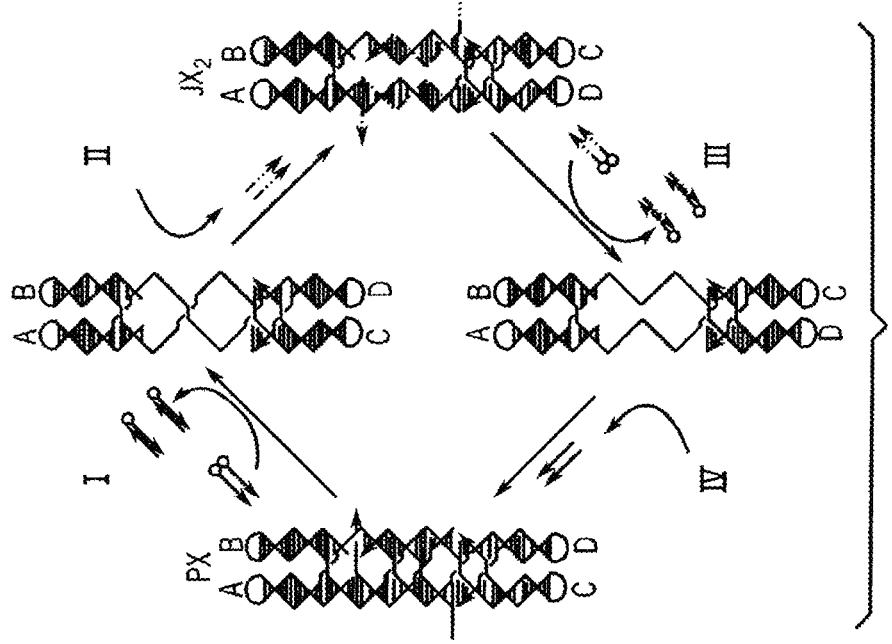
FIG. 10A
FIG. 10B

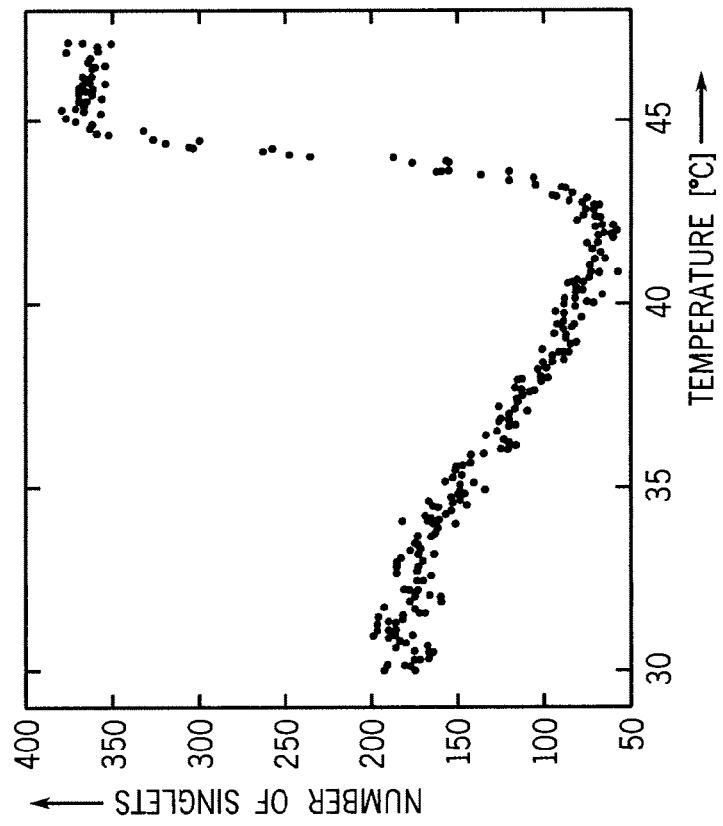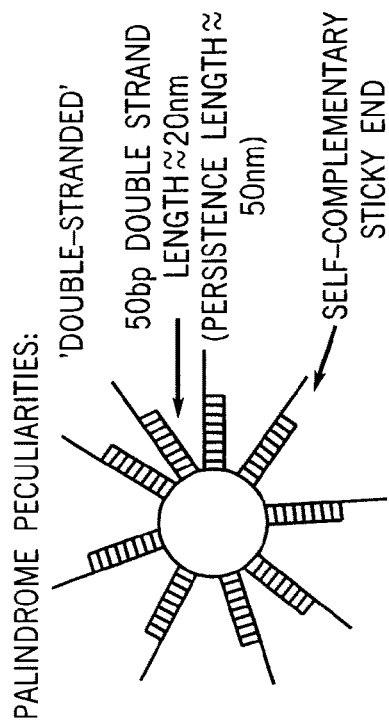
FIG. 25

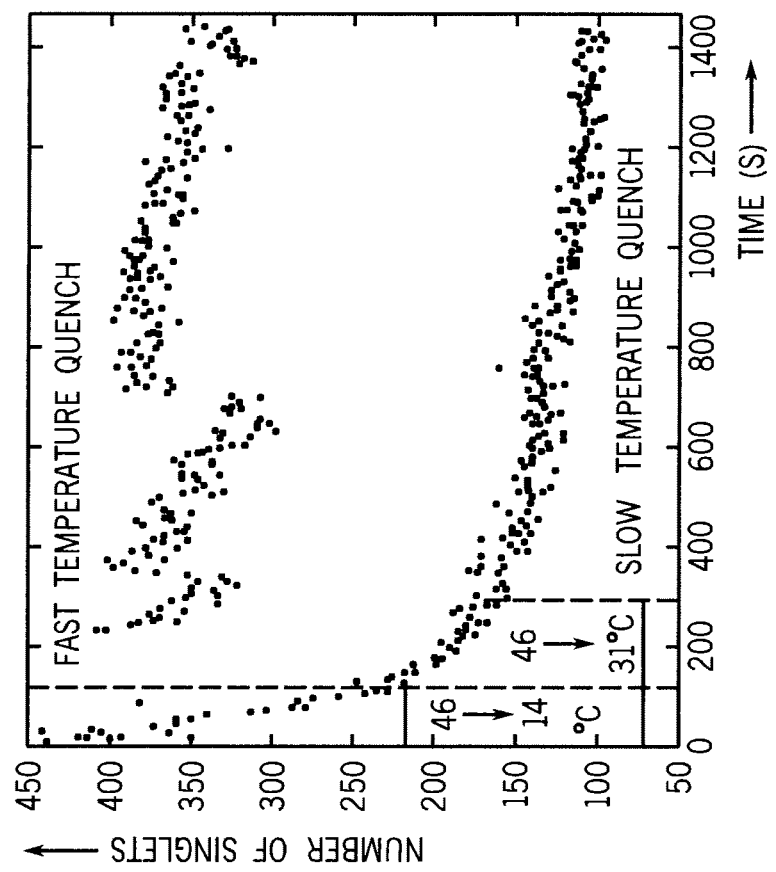
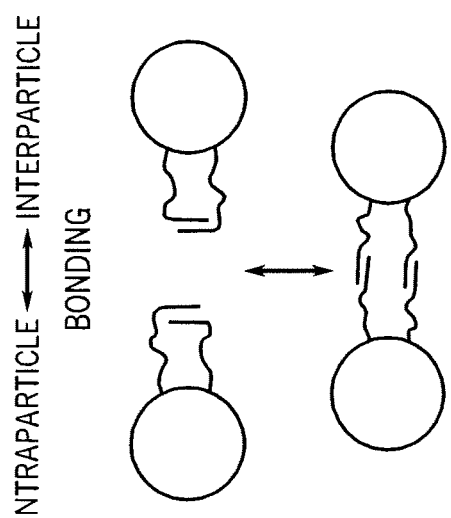
FIG. 26

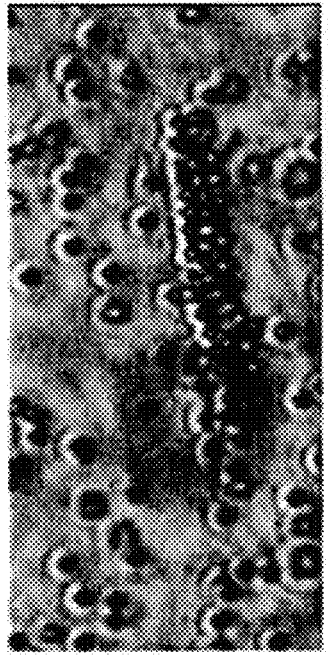
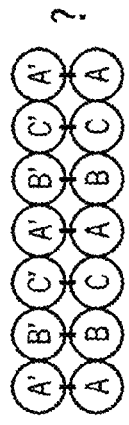
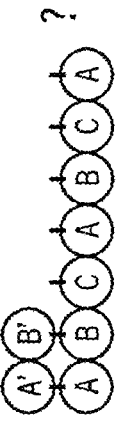
FIG. 28

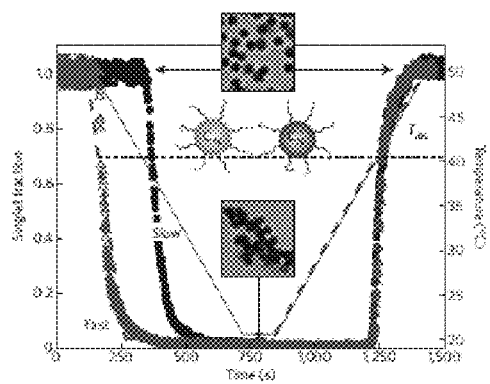
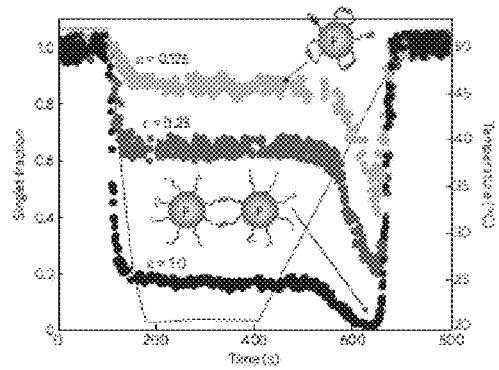
FIG. 30aFIG. 30b
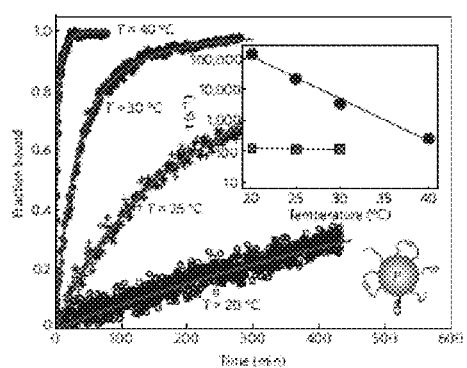
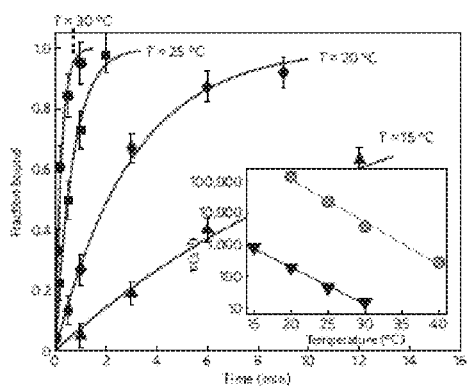
FIG. 31aFIG. 31b

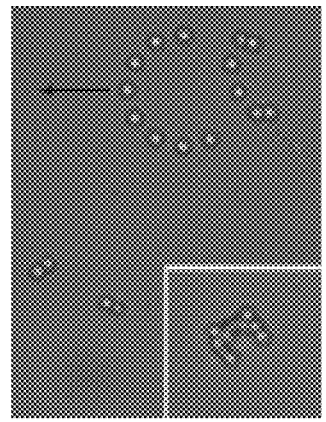 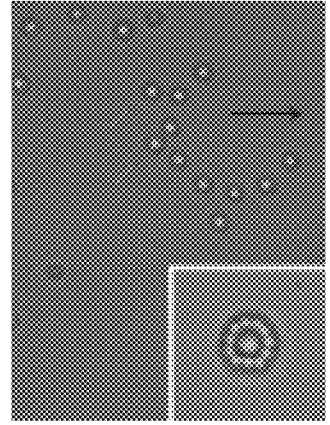
FIG. 32a        FIG. 32b
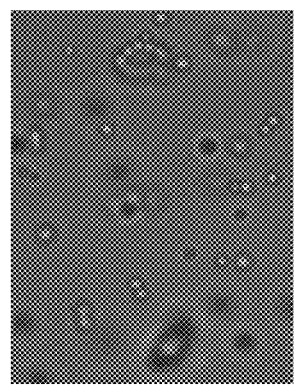 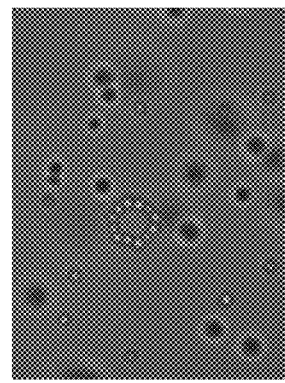
FIG. 32c        FIG. 32d FIG. 32e(1) 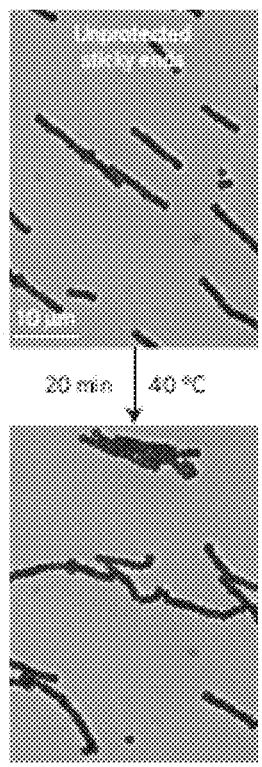
FIG. 32f(1) 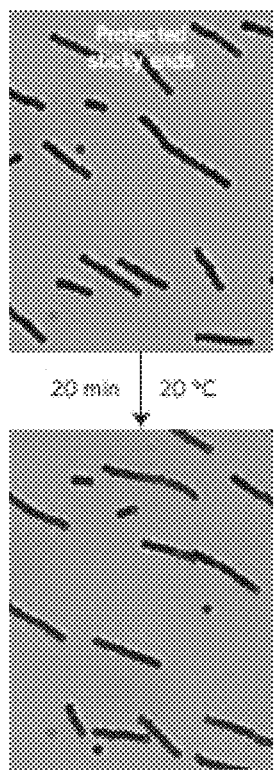
FIG. 32g(1) 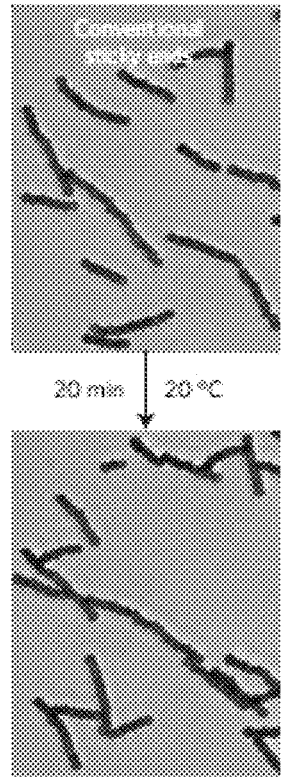
FIG. 32e(2)
FIG. 32f(2)
FIG. 32g(2)

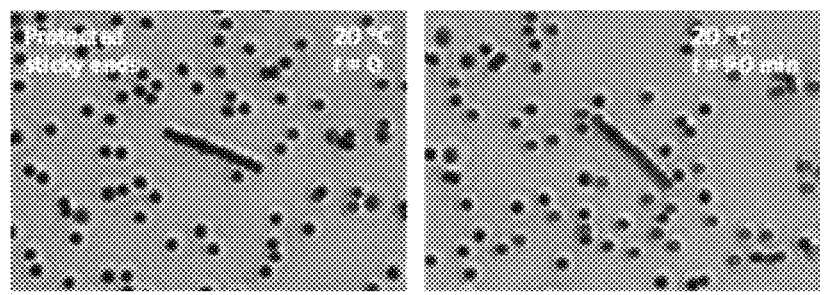
FIG. 32h(1)          FIG. 32h(2)
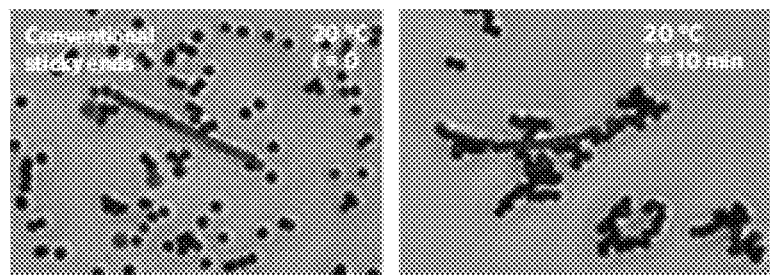
FIG. 32i(1)          FIG. 32i(2)

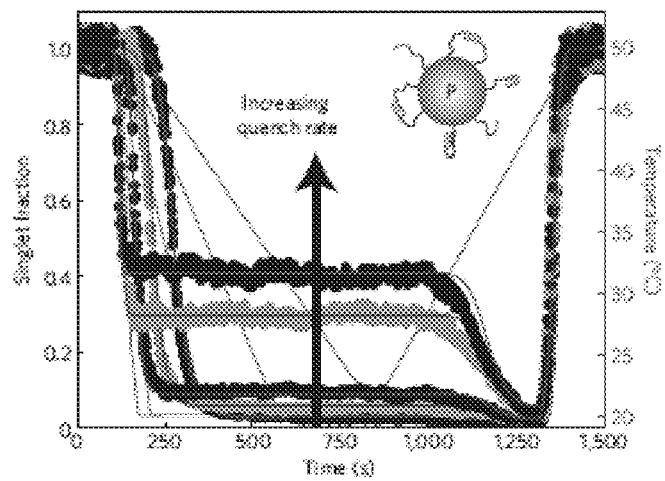
FIG. 33a
FIG. 33b(1)  FIG. 33b(2)

SELF-REPLICATING MATERIALS

CROSS REFERENCE TO RELATED APPLICATIONS

This application is a Continuation-In-Part of PCT Application No. PCT/US2007/025749, filed Dec. 17, 2007, incorporated herein by reference in its entirety, which claims priority from U.S. Provisional Application 60/875,272, filed Dec. 15, 2006, incorporated herein by reference in its entirety. This application claims priority from U.S. Provisional Application 61/182,597, filed May 29, 2009, incorporated herein by reference in its entirety.

SEQUENCE LISTING

The instant application contains a Sequence Listing which has been submitted via EFS-Web and is hereby incorporated by reference in its entirety. Said ASCII copy, created on Nov. 5, 2009, is named 04643401.txt, and is 3,683 bytes in size.

BACKGROUND

Technological advances allow the manipulation of extremely small units of matter, even individual atoms, opening up the possibility of macrofabrication technologies. Such technologies could be used to design nano and micro-scale machines, or to accurately control individual elements in larger materials or machines. Practical realization of these technologies is blocked by the inability to adapt experimental and small scale techniques to the larger scales required of industrial production. Conventional materials production is a linear process. Doubling the amount of material created requires twice the production time. Linear scaling of production is a critical problem if the goal is to create useful, i.e. macroscopic, quantities of microscopic building blocks with sophisticated internal structures.

Exponential growth is the most elegant and effective solution to the problem, as demonstrated by biological systems, in which a single cell generates offspring which themselves can build more copies. A single cell containing the necessary information can also divide and develop into a living organism, demonstrating that large, complex systems can be built and operated from self-reproducing units. While nature teems with organisms that readily reproduce, no one has yet succeeded in making an artificial material that can repeatedly copy itself. Making a material which self-replicates presents not only a significant scientific challenge but also the potential for applications which bridge the microscopic and macroscopic worlds. Self-replication leads to exponential growth providing a practical means to scale up production of components for nanomachines and larger scale more functionally complex assemblies. Demonstrating self-replication and developing the science behind it therefore represents an important step for nanotechnology and for enabling the practical development of the technology.

SUMMARY OF THE INVENTION

The invention encompasses, inter alia, an artificial composition capable of replication, methods of constructing and replicating such compositions, methods of creating novel materials by use of such methods and compositions, and the novel materials so made.

In one embodiment, the invention is a replicable artificial composition, comprising:

(a) at least two particles, $P_1$ and $P_2$, bound together,
(b) a surface-exposed first and second chemical moieties $A_1$ and $A_2$, which are able specifically and reversibly interact with chemical moieties $B_1$ and $B_2$; wherein one of said $A_1$-$B_1$ and $A_2$-$B_2$ interactions can be modified to make the A1-B1 interaction irreversible under conditions in which the $A_2$-$B_2$ interaction is reversible. Suitable particles may be any macromolecule. In some embodiments, the particles are colloidal particles, which may be composed of a polymer, a metal, a glass, a ceramic, a crystal, for example. Particles may be uniform in some embodiments. In other embodiments, the particles are nonuniform at their surface (patchy). Patchy particles allow, in some embodiments, directionality in the relationship with other particles.

Interactions between the particles are governed, at least in part, by chemical moieties that are present on the surface of the particles. Such chemical moieties may be inherently part of the particle, or added as a coating. In exemplary embodiments, such chemical moieties comprise DNA or other nucleic acid. In exemplary embodiments, suitable DNA sequences comprise a sequence selected from the group consisting of: CCATGCGCATGG (SEQ ID NO: 1); AGCATGCATGCT (SEQ ID NO: 2); AGCTGTCAAGGA (SEQ ID NO: 3); GCCTCTGAGAGA (SEQ ID NO: 4); and the complement of any one such sequences. In some embodiments, the DNA sequences are palindromic.

Interactions between particles can also be moderated by other factors. For example, the surface of the particle may also contain, or be modified to contained, additional molecules that minimize the effect of van der Waals forces between particles. Polymers such as polyethylene block copolymers are useful in this regard. Particle interactions can be modified by additional chemical and physical forces, including pH, ionic strength, charge, temperature, concentration, magnetic fields, electrical fields, gravitational fields, photons and waves, and gradients of temperature, charge, magnetic field, concentration etc. Temperature is especially useful in this regard.

Interactions may be formed and reversed under different conditions. Interactions can be made irreversible by, for example, making reversibility dependant on a condition that is not provided. Reversible interactions between moieties can also be made irreversible by the formation of chemical bonds between such moieties, especially covalent chemical bonds. Exemplary chemical bonds includes disulfide bonds, amine, amide and ester bonds, etc. In one embodiment, the interaction between complementary strands of DNA is made irreversible by the addition of an intercalating agent, such as psoralen, and the addition of energetic particles that cause said complementary strands of DNA to cross link, and thereby create a covalent bond between strands.

The type of artificial compositions suitable for replication are not limited in terms of the number of particles, the shape or size of the particles, or the spatial relationship between the particles. Thus, an artificial composition suitable for replication may be linear, planar, or three dimensional.

Another aspect of the invention includes methods of making an artificial composition capable of replication, which is used as a seed for the replicative copying. Such artificial compositions may be made with the assistance of optical tweezers, holographic optical traps, magnetic fields, electrical fields, gravitational fields and the like. In one embodiment, the seed comprises at least at least two particles, $P_1$ and $P_2$, bound together, which possess surface-exposed first and second chemical moiety, $A_1$, $A_2$, wherein $A_1$ and $A_2$ may be the same or different, and are suitable for directing interactions with particles that are not part of the seed.

Holographic optical traps are particularly useful for directing the spatial relationship between particles in one, two and three dimensions.

Another aspect of the invention is a method of copying such an artificial composition by a replicative process. A method of making a copy of an artificial composition, comprising constructing a seed particle comprising at least two particles, $P_1$ and $P_2$, bound together with a surface-exposed first and second chemical moiety, $A_1$, $A_2$, wherein $A_1$ and $A_2$ may be the same or different. The seed particle is exposed to (a) at least one third particle $P_3$ comprising at least a third surface-exposed chemical moiety B, wherein $A_1$ B specifically and reversibly interact, and at least a fourth surface-exposed chemical moiety C, wherein C specifically and reversibly interacts with a fourth chemical moiety D, wherein C and D are the same or different, and to (b) at least one fourth $P_4$ particle comprising the surface-exposed chemical moiety D, and a surface-exposed chemical moiety F, wherein F specifically and reversibly interacts with $A_2$. The seed of $P_1$ and $P_2$ and the particles $P_3$ and $P_4$ are mixed under a first condition favorable for specific and reversible $A_1$-B, $A_2$-F, and C-D interactions. Next, a second condition is applied that causes the C-D interactions to become irreversible under at least a third condition, wherein said third condition reverses $A_1$-B and $A_2$-F interactions. When such third condition is provided, the $A_1$-B and $A_2$-F interactions are reversed, but the C-D interactions are not. The result is that the particles $P_3$ and $P_4$ are associated such their relationship replicates that between $P_1$ and $P_2$, thereby copying the seed. This method can be repeated, producing more copies of the seed. Preferably, the daughter of each replicative event (e.g. $P_3$-$P_4$) is suitable for use as a seed for further replication, thereby achieving exponential growth of the replicable composition. The above method can be practiced with any of the particles, chemical moieties, DNA sequences etc. as are defined elsewhere herein.

In another aspect, the invention comprises materials made by the above methods. Because the invention provides means for generating multiple copies of particles in a particular arrangement, the invention is useful for creating designed components for nano- and micro-scaled machines, and materials with novel properties. For example, the presence of certain elements (such as particles susceptible to variation in charge, energy state etc) can be controlled. Accordingly, the present invention provided methods for making materials such as photonic crystals, silicon wafers, and the like.

BRIEF DESCRIPTION OF THE DRAWINGS

FIG. 5 illustrates the use of optical tweezers to construct, from two different colloidal beads, a specific arrangement of beads.

FIG. 6 shows the basic replication scheme. FIG. 6A shows a schematic diagram of a linear seed comprising two types of particles, A and B, which are first arranged and then permanently bound through the use of psoralen and UV light. FIG. 6B shows complementary particles specifically binding to particles in the seed, using the presence of complementary DNA species. FIG. 6C shows a completed complementary daughter strand. After treatment with psoralen and UV, the daughter strand becomes cross-linked. There is no crosslinking, however, between the DNA strands that direct the association between the seed and daughter strands, because the DNA species lack AT pairs. The result (FIG. 6D) is that when the temperature is raised, the seed-daughter interaction is reversed, but not the interaction between the particles within a seed, or within the daughter. The result is that the daughter strand has copied the seed.

FIG. 10a shows the machine cycle of the PX-JX2 nanomechanical device and 10b shows a system of DNA trapezoids connected via the device that make its action visible under the AFM.

FIG. 25 shows aggregation of particles containing palindromic ends

FIG. 26 Intraparticle bonding versus interparticle bonding can be controlled by the rate of temperature quenching.

FIG. 28 AFM of a linear seed with a palindromic sequence in a bath of particles with complementary sticky ends, forming daughter strands. Diagrams illustrate the problem of particle seed interactions in which the singlet particles prefer to reside in the interstices of the seed, and bind to two adjacent particles. This results in disruption of the correct spacing of the particles in the daughter strand. One solution is to provide at least 3 different beads (flavors) so that there are no favorable interstices. Another solution is to assemble the complementary daughter strand in linear manner, relying on the previous correct positioning of the preceding particle in the daughter strand.

FIGS. 30a and 30b show association-dissociation kinetics for conventional and self-protected interactions; FIG. 30a is a plot of the temperature (in red) and the corresponding particle singlet fraction (symbols) as a function of the elapsed time, for conventional interaction scheme 1a; the solid red line and black dots correspond to the slowest temperature quench; the dashed red line and blue triangles correspond to the fastest quench; the microscopy insets show a small part of the sample; FIG. 30b shows a particle singled fraction as a function of time for self-protected interaction scheme 11 and a fixed temperature profile, but at different overall particle concentrations (c=1.0 corresponds to ~2.8×10$^{11}$ particles per square meter);

FIGS. 31a and 31b show temperature response and proximity response of the switchable self-protected interactions. FIG. 31a shows a fraction of aggregated scheme 11 particles as a function of time at different temperatures; the inset shows the characteristic aggregation times τ (black dots), obtained by fitting the data with the Smoluchowski aggregation equation, $f_{bound}(t)=1-(1+t/\tau)^{-2}$; the τ values for conventional interaction scheme 1a are also shown (green squares); the error bars are approximately the size of the symbols; FIG. 31b shows a plot of the fraction of scheme 11 particles that remained bound after keeping them close together in a weak magnetic field (~1 mT), for different field exposure times (horizontal axis) and temperatures; the inset shows the characteristic association time r (black triangles), as obtained from first-order kinetics, $f_{bound}(t)=1-\exp(-t/\tau)$; the diffusive aggregation times of the scheme 11 beads in a are reproduced in grey; and all error bars result from the uncertainty in the singlet fraction obtained from image analysis;

FIGS. 32a-32i show directed assembly using self-protected interactions as a 'nano-contact glue'; FIG. 32a shows a microscopy image of scheme 11 particles in a circular array of optical traps, at high temperature (T≈27° C.); the black arrow indicates a displacement of the array, causing the release of two accidentally formed doublets (red arrows); Inset: Example of the disordered clusters that were obtained at high temperature in a rotating ring trap; FIG. 32b shows as in FIG. 32a, but at low temperature (T≈20° C.); displacement of the array releases superfluous particles from doubly occupied traps (red arrows), without forming unwanted doublets; Inset: a properly formed ring structure from a rotating ring trap at low temperature. FIG. 32c shows after 20 min at 27° C., multiple suspension particles stuck to the previously assembled ring structure (red arrows); FIG. 32d shows this does not happen at low temperature (20° C.). FIGS. 32e and 32f (1 and 2) show linear chains of scheme 11 particles, made with magnetic traps, were kept for 20 min at T=40° C. (FIG. 32f (1 and 2)); FIG. 32g (1 and 2) shows the results of a similar experiment with conventional sticky ends, which cannot form protective secondary structures; FIG. 32h (1 and 2) shows a linear chain of scheme 11 particles was isolated and transferred to a new suspension of the same particles, after which it was kept inert for a prolonged time at low temperature (20° C.); FIG. 32i (1 and 2) shows the results of a similar transfer experiment with conventional DNA-functionalized particles; and the original chain is shown in red; in all images, the particles were ~1.0 μm in diameter; and FIGS. 33a-33e show experimental and modelled association-dissociation kinetics; FIG. 33a shows experimentally recorded particle singlet fraction (dots) as a function of time for self-protected interaction scheme 11 and different temperature ramps (in blue); the red lines show the fits from our theoretical model. FIG. 33b shows our nomenclature for the different hybridization possibilities on an isolated scheme 11 bead (1) and for two such beads in contact (2); FIG. 33c shows calculated bond distributions on an isolated scheme 11 bead, as a function of temperature; FIG. 33d shows in FIG. 33c, but for two beads in contact; FIG. 33e shows a plot of the temperature (in red) and the corresponding particle singlet fraction (symbols) as a function of the elapsed time, for interaction scheme 1b of FIG. 29; and the solid red line and black dots correspond to the slowest temperature quench; the dashed red line and blue triangles correspond to the fastest quench.

DETAILED DESCRIPTION OF THE INVENTION

Figure 1:
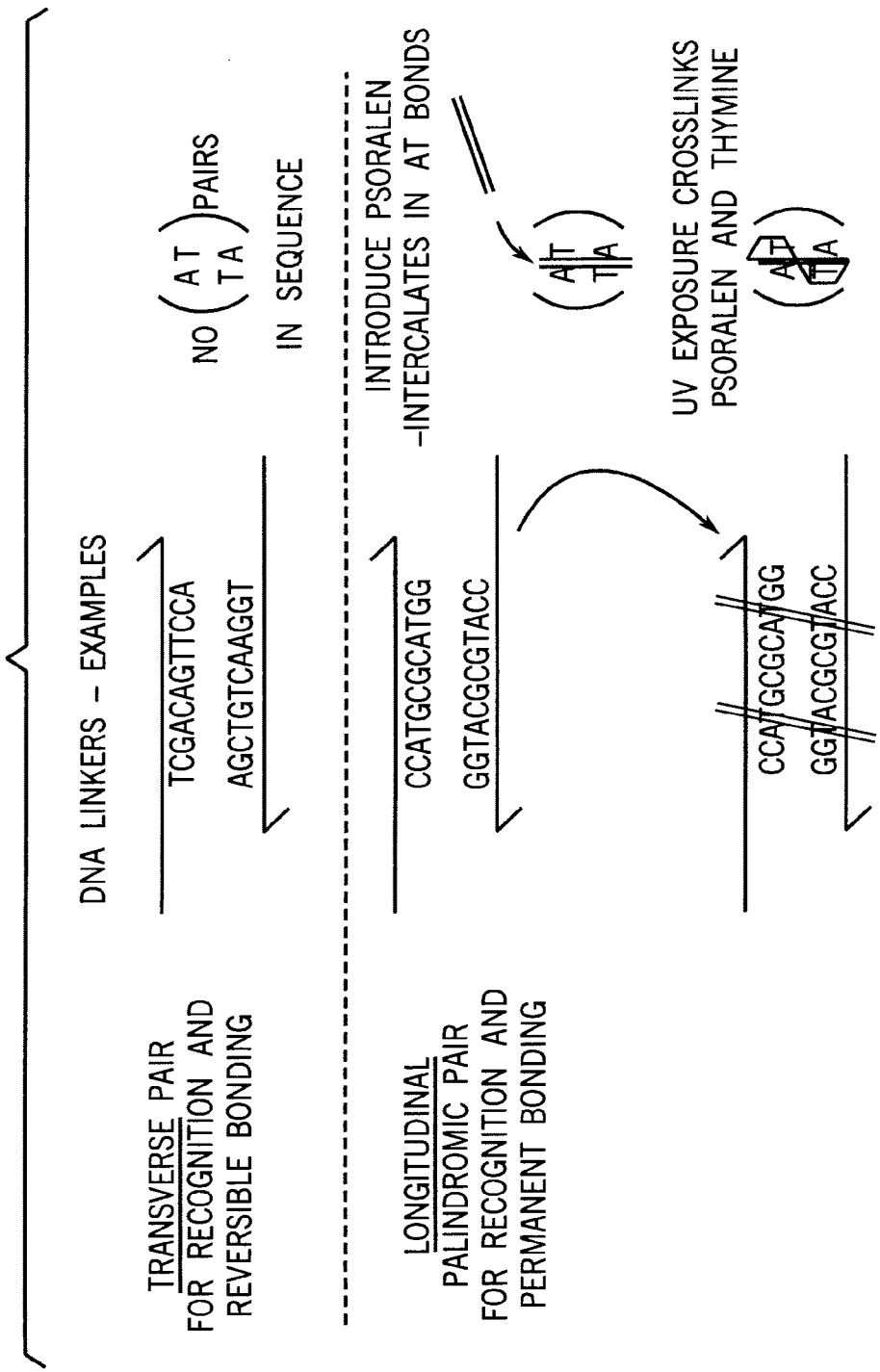
FIG. 1 demonstrates how exemplary DNA sequences can be used to control particle interactions. DNA sequences interact with complementary sequences, permitting specific and reversible interactions. Certain interactions can be made irreversible. For example, when the compound psoralen is added to DNA, and then exposed to UV light, the psoralen cross-links between thymidine in complementary A-T pairs, thereby chemically binding the complementary strands. Sequences lacking A-T pairs are not cross linked. Therefore, sequence selection can be used to control whether a given interaction is reversible or not. DNA linkers disclosed as SEQ ID NOS 6, 1, 1, 1 & 1, respectively, in order of appearance.

Self-replicating materials were created by first to constructing a single complex microscopic structural unit—a seed—with a specific internal structure, and then subjecting it to a cyclic process by which it self-replicates and produces, after a relatively short time, a macroscopic number of copies of the original. The original and its copies are designed to subsequently self-assemble into more complex structures.

Self-replication and self-assembly requires that each elementary unit encode information in terms of chemical (short range, specific) and physical properties. It further requires a means to read this information, by interacting with other particles. The chemical and physical interactions then lead to recognition, specific attractions, repulsions and arrangement into specific configurations. Self-assembly and self-replication is therefore guided by information coded into elementary units or building blocks. Single atoms and simple molecules interact with each other in simple ways; lacking the rules to encode sophisticated structures, they organize in only a few simple motifs. As the units become more complex and contain more information, the number of structures they form increases. The more information that is encoded in the building blocks the more sophisticated the resulting structure.

The present invention demonstrates replicative assembly of colloids to which is attached specific DNA linkers. Specific DNA chemical links and electrostatic and magnetic interactions are varied, in a cyclic process. In each cycle the pattern is recognized, copied, fused, and separated from its parent. With colloidal particles, for example, it is possible to control the information encoded in their interactions in the form of short strands of single stranded DNA molecules grafted onto their surface. The DNA molecules which are used specifically recognize complementary DNA molecules grafted to other colloids, which can be made to bind or unbind by changing the temperature. An important feature is that many different complementary DNA pairs can be grafted on different types of particles so that, for example, A type particles coated with one type of DNA can be made so that they bind only to A' type particles coated with DNA strands complementary to those on A. Similarly, B-B' type particles with different complementary strands on their surfaces can be prepared such that B particles stick to B' particles but A and A' particles do not stick to B or B' particles.

A particle or macromolecule contains, or is modified to contain, molecules that direct the interaction of said particle/macromolecule with other particles/macromolecules. Particle interactions are determined by (a) varying the molecules on a given first particle (b) varying the molecules on second and subsequent particles and (c) controlling the physical and chemical environment, and the temporal sequence to which particles interact.

For example, in one embodiment, a micrometer scale ($10^{-6}$ m) seed consisting of different kinds of colloidal particles permanently is linked together into a particular identifiable motif. The seed is introduced into an aqueous bath containing an unbound stock of colloidal particles. Replication of the seed proceeds by a process of cyclic temperature and light intensity variations in which the seed is used as a template to assemble copies of itself from the bath of stock particles. After 10 doubling cycles, there is about $10^3$ replicas of the original bath; after about 50 doubling cycles, there is approximately $10^{14}$ replicas of the original seed, which would fill a liter-size container. The system is highly flexible, working effectively with different seeds and motifs designed to interact and self-assemble into different structures and devices In some embodiments, the particles/macromolecules are colloidal particles. Colloidal particles with different sizes, shapes (e.g. round, convex, elongated etc) compositions (polystyrene, other polymers, ceramics, metals, dielectric materials, glasses, biological macromolecules, etc) are known, spanning a range of physical properties. The invention is not limited to particles with similar physical properties, but is also effective with highly heterogenous seeds composed of particles with different compositions (e.g. polymers, ceramics, metals, etc) and different physical and chemical properties. Amplification of these seeds then allows for controlled separation and segregation of the stock particles from the bath. The seeds may then be used in their prepared form, or the segregated particles may be processed in different ways, to form two or three dimensional structures.

The present invention functions particularly well in colloidal systems. Colloidal suspensions, which consist of micrometer-size particles suspended in a liquid (e.g. water) allow the person of ordinary skill in the art to (1) control their chemistry and interactions, (2) precisely position different kinds of colloidal particles into virtually any pattern using optical tweezer arrays, (3) label them with fluorescent dyes to observe and identify different particles under optical microscopes, and (4) because their dynamics are sufficiently slow, to track their movements, measure their interactions, and follow chemical reactions between them under an optical microscope. Thus, in developing specific self assembling units, virtually every step of the self-assembly and self-replication process can be observed in considerable detail. Colloidal systems can then be used directly, or adapted to both larger and smaller scales, down to nanometer size building blocks.

The invention allow exploitation of the specificity of these DNA-mediated interactions to directly program the self-replication and self-assembly of colloids and, because different colloids can be fluorescently labeled and observed under a microscope, to monitor, visualize, and record in real time the reactions, configurations, intermediate states, mistakes, products, and competition that occur during self-assembly and replication.

The colloidal system is ideal for demonstrating, understanding, and debugging any new processes. It is also a means to directly produce structures, sensors, actuators, reactors, and materials on a micrometer to macroscopic length scale. Accordingly, the processes are extended to the nanometer scale using polymers and nanoparticles to produce active structures and patterns for the submicron world.

The invention introduces a new class of materials and devices built from programmed microscopic building blocks. In another aspect of the invention, depletion type forces and depletion zones can be utilized in the implementation of the self assembly and self replication of materials, including without limitation colloidal particles.

The invention also provides for means to monitor errors in reproduction, and identify ways to control such errors. In some situations, errors are to be avoided. In others, errors can be advantageously used to develop new structures by a process analogous to mutation and selection seen in nature.

Methods of Preparation

1. Preparation of particles. Polystyrene colloidal particles about 1 micrometer in diameter are commercially available. DNA can be attached to their surfaces by, for example: (1) by directly grafting PEG-DNA strands onto carboxylate surface groups on in-house synthesized particles or (2) by using commercially available particles functionalized with streptavidin together with biotin-terminated DNA strands that irreversibly bind to the streptavidin. Fluorescently-labeled particles can also be purchased or prepared in-house.

A core-shell dying technique is then used to provide better optical resolution. Different polymer brushes are also used to suppress non-specific binding and optimize reversibility. The DNA sequences are also modified to optimize information storage. A key element is functionalizing the particles with two DNA linkers Paramagnetic cores for aligning the particles in a magnetic field, use directional, "patchy" particles for increased specificity and for branching into more complex chains.

2. Characterize single pair particle interactions, binding, and dynamics. Interactions between particle pairs can be measured directly using laser optical trapping techniques. Measurements of melting curves for different sequences and in different buffer solutions are also used to further characterize the interactions and to precisely tune the melting temperature between particles coated with various complementary sequences of DNA. The reaction kinetics, including reaction rates and particle transport are characterized using optical microscopy. Together, this suite of measurements enables optimization of the cyclic processes of assembly, binding, and melting.

3. Fabrication of seeds—particle motifs and sequences. Holographic optical traps (HOTS) are used to assemble arbitrary sequences of particles to create seeds of any desired design (i.e. a specific sequence of A and B particles).

Sequences of particles in a chain are bound irreversibly by the addition of psoralen and subsequent exposure to UV light. Psoralen intercalates into DNA possessing complementary TA pairs. Psoralen is also highly absorbent of UV, and DNA-intercalated psoralen will mediate DNA cross linking in the presence of UV. Because this cross-linking results in a covalent chemical bond between complementary strands, the strands will not completely separate under conditions suitable for strand separation, like raised temperature.

DNA lacking a TA pair will not intercalate psoralen and so will be resistant to UV-mediated crosslinking. Therefore, any particle can possess DNA that will cross link in the presence of psoralen, and DNA that will not.

In one embodiment, the particles in a chain possess palindromic sequences which permit bonding to the same sequence on other particles. The person of ordinary skill in the art can determine the UV dosage required for fixing with psoralen and the rigidity of the chains that results.

The use of magnetic particles and an external magnetic fields is also useful for arranging particles, such as by aligning them within a field, especially when the particles are in a chain.

4. Interaction of complementary particles with a seed chain. Interactions and reversible binding of single particles, with their complementary particles on a seed, occurs in a fluid containing an excess of free single particles. Most typically, temperature is used to control the rate and strength with which particles attach to one another. The person of ordinary skill in the art can determine the temperature dependence of the particle association with a seed, its kinetics, sticking time, etc. Also determinable by the person of ordinary skill is the dependence on position within the seed chain of a particle sticking to one of its complements.

A magnetic field may also be used to align the single complementary particles in a line along the seed chain. Coordinate use of magnetic fields and temperature are used to control alignment and hybridization together, especially in the formation of higher order structures.

Another important factor in hybridization between the seed and daughter particles is the problems of suboptimal arrangements that cause elemental defects, such as vacancies, kinks, and mispairing (nonspecific binding). Nonspecific binding and other defects are controlled by appropriate control of temperature, magnetic field, and temporal factors, as well as the design of the particles, thereby forming a daughter chain that faithfully duplicates the sequence of A and B particles on the seed.

5. Demonstration of duplication. Once daughter chains are assembled, they are permanently cross-linked by intercalation of psoralen between complementary TA pairs of DNA on neighboring particles and then exposure to ultraviolet light. UV dosage must be sufficient to cause cross linking; but excessive UV can cause undesirable damage to DNA, and particles. Once permanent links between particles in the daughter strand are formed, raising the temperature will melt the DNA bonds between the seed and daughter strands, causing the daughter seed to lift off, thereby causing the replication.

6. Exponential Growth. The final step in achieving self-replication is repeated cycling of the replication process, such that the daughter strand from process N is available as a template strand for all N+1, N+2, etc. Replication systems are monitored to measure the yield as a function of cycle number, the sensitively of replication rates, fidelity, and yield and how these depend on the replication cycle parameters, such as temperature, magnetic field, their timing (e.g. phasing), etc.

7. Competition and Evolution. Once exponential growth is achieved, evolution and mutation can be used to further optimize replicative process. For example, different seeds can be introduced, and allowed to compete for particles. Thus, it is possible to see how each seed grows, which grows faster, and whether one wins. In a similar vein, it is possible to determine how errors propagate and compete under exponential growth conditions. Errors may occur under normal operating conditions, but may be enhanced under particular conditions, for example by putting in chemicals that preferentially attack a particular DNA bond or by starving the bath of one of the components in the seed. Ordinarily, high fidelity in copying is desirable. However, the introduction of errors and subsequent evolution may be advantageously applied to develop new replicating materials.

Self-Replication of DNA Coated Particles

As outlined above, it is now possible to make a large number of identical strings of colloidal particles of some specific motif, say ABABBA, by starting with a single string and then making many copies using exponential growth. For a single string to maintain its integrity, the particles must be permanently linked within a single strong. However, to make copies of a string, single A and B particles from the bath must first recognize and at least temporarily bond to particles on an existing string. Once the proper sequence (ABABBA in this example) of particles from the bath has attached to an existing string, the particles in the new string are bonded together in a two stage process: first, temporarily and then, when the new string is completely formed, a signal is sent causing them to bond together permanently. All temporary bonds are formed using DNA hybridization; in some cases, these temporary bonds are augmented by attractive magnetic interactions. Permanent chemical bonds are formed using psoralen as a chemical linking agent using a scheme described below.

There are several parts to the replication process. In the subsections below, we describe various parts of the process, not in the order they are used but in terms of the concepts required to comprehend the entire process. Once we have described each of the processes, we are then in a position to describe the detailed protocol by which the replication process proceeds.

1. Particle Recognition and Binding Scheme Using DNA

Particle recognition is determined by chemical moieties designed to interact with a complementary moiety. As outlined above, such interaction should be both specific and reversible. The chemical interactions between strands of DNA are well understood, are reversible. DNA is also a stable molecule. Thus, in one embodiment, hybridization between strands of DNA are used to direct particle-particle interactions.

The colloidal particles for our replication scheme ("Plan A") actually consist of four different kinds of polystyrene particles, A, A', B, and B' distinguished by the combinations of DNA grafted to their surfaces (N.B. there are two kinds of A and two kinds of B particles). The beads have small paramagnetic particles embedded in them so that in a magnetic field of 20 mT they align into single strands. The recognition and bonding of the beads to each other are determined by the DNA sequences, colloquially referred to as "sticky ends." Each kind of particle has two different types of DNA molecules grafted to its surface, one to facilitate bonding along a chain for string formation—longitudinal bonding—and another to facilitate bonding between different chains for copying—transverse bonding.

FIG. 1 shows schematically the two types of DNA sequences suitable for use for longitudinal and transverse interactions (in an exemplary embodiment). The transverse sticky ends form a Watson-Crick complementary pair. The longitudinal sticky ends form a pair from identical sequences that are self-complementary (forming an "inverse palindrome" since the first half base-pair sequence is the complement of the second half). The longitudinal links also have A-T/T-A neighbor bonds. A small aromatic molecule, psoralen, can intercalculate between these bonds. When excited by UV radiation, it chemically bonds to the thymine (T) groups producing a permanent cross-link between the sticky ends (see lower part of FIG. 1).

Figure 2:
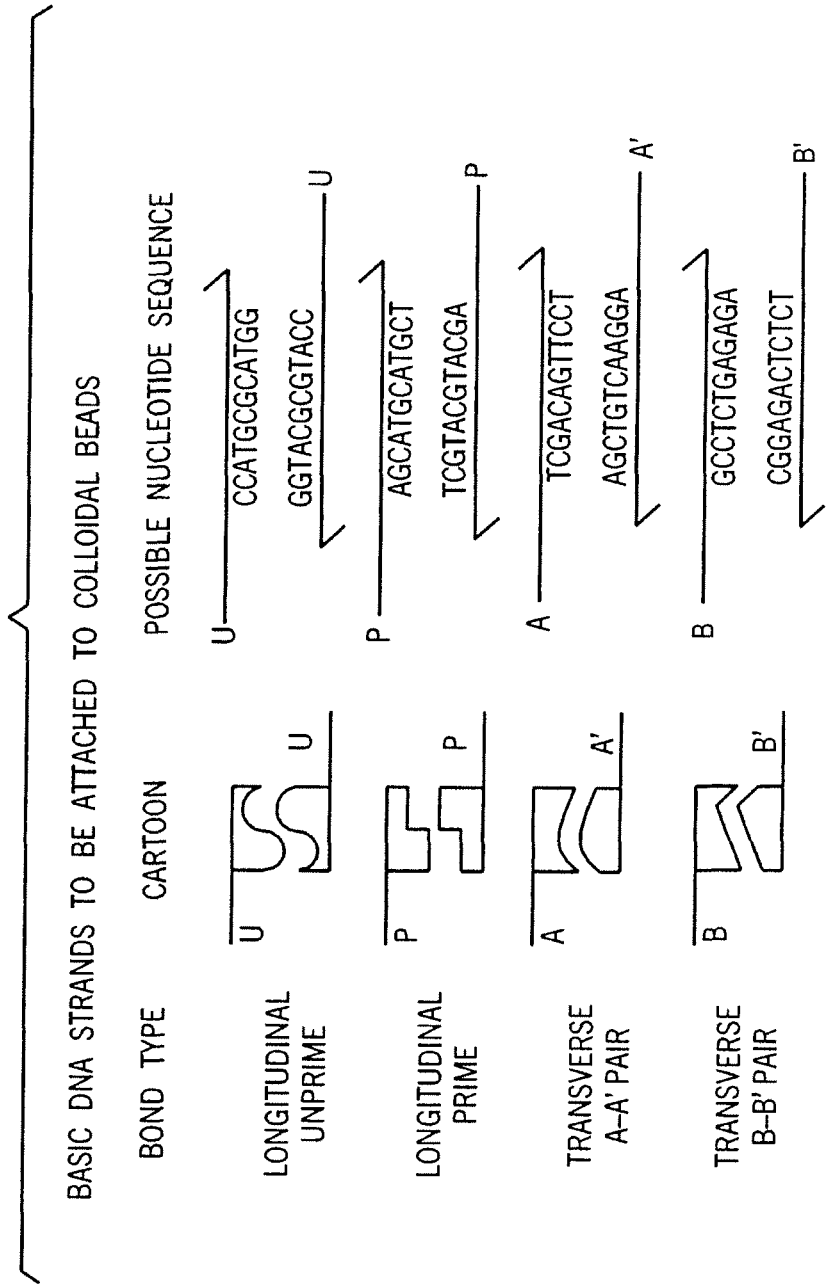
FIG. 2 illustrates complementary pairs of DNA sequences used in subsequent figures (SEQ ID NOS 1, 1, 2, 7 & 4, respectively, in order of appearance).

FIG. 2 illustrates schematically a set of sticky ends. There are two self-complementary palindrome sequences U and P and four other sequences in two sets of complementary pairs A-A' and B-B'. (Here we use non-italicized symbols A, A', B, and B' to refer to the DNA sequences while the italicized symbols, A, A', B, and B' refer to the respective particles to which these DNA sequences are attached).

Figure 3:
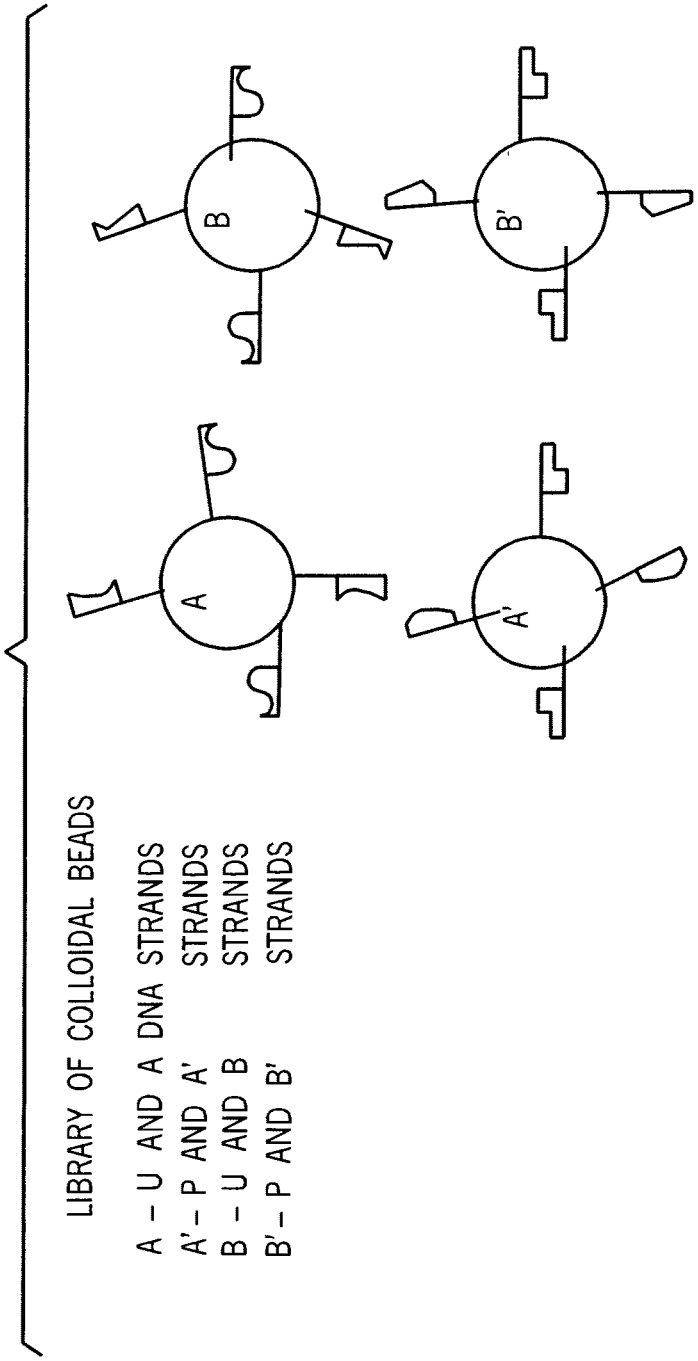
FIG. 3 illustrates colloidal beads, each of which contains different collections of complementary DNA strands and therefore direct the interaction between different beads.

FIG. 3 catalogs the four starting colloids that will be present in our stock bath and which will be used in the seed and daughter chain motifs. Beads A and B have palindrome U DNA sequences that bind to each other. Thus, A-A, B-B and A-B bonds can be formed by hybridization of the U palindrome DNA sequence on these "unprimed" spheres, thus enabling "longitudinal" bonding. These bonds can be made permanent with psoralen and ultraviolet exposure. There is also a distinct P palindrome DNA sequence attached to the A' and B' particles that can similarly permanently link the "primed" particles A'-A', B'-B' and A'-B'. Both palindrome sequences U and P have A-T/T-A units that enable permanent bonds. The DNA sequences U and P are designed specifically to avoid U-P hybridization.

Figure 4:
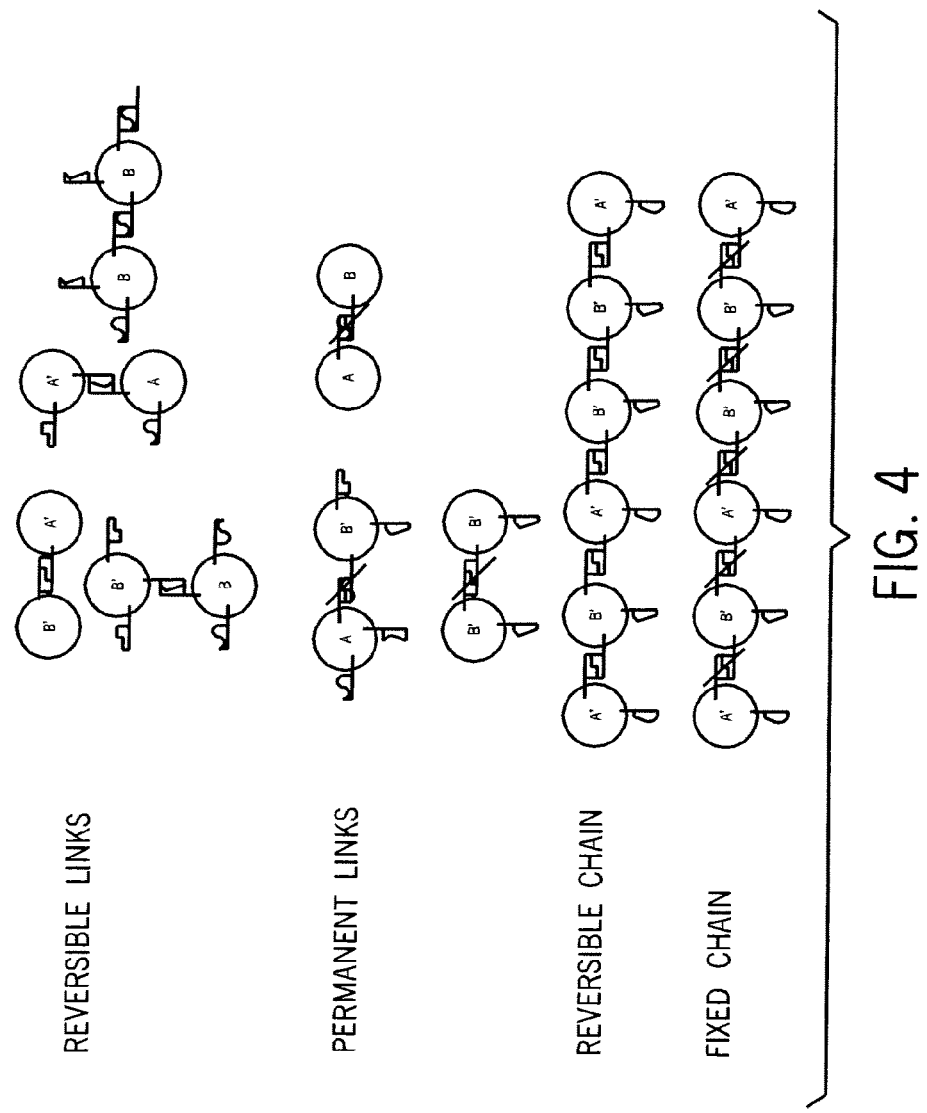
FIG. 4 summarizes the kinds of reversible and permanent links that can be made between the four differently functionalized colloidal particles A, A', B, and B'.

A different set of DNA sequences implements recognition and reversible assembly—the transverse bonds. The Crick A sequence is attached to particles A; the complementary Watson sequence A' is attached to particles A'. Similarly the Crick B and complementary Watson B' sequences are attached to their respective beads, B and B'. The DNA sequences U and P do not hybridize with each other and the DNA sequence A' does not hybridize with the sequences B, B', U, or P. It only hybridizes with A at temperatures above ~15 C. This behavior is confirmed and optimized through direct measurements of the particles' temperature-dependent interactions. FIG. 4 summarizes the kinds of reversible and permanent links that can be made between the four differently functionalized colloidal particles A, A, B, and B'.

In other embodiments, chemical linkages are also not limited to DNA-DNA interactions. Other nucleic acids can also be used, for example. Artificial forms of nucleic acids, such as PNA are typically more resistant to degradation by enzymes and have stronger binding to target sequences. Other reversible biological linkages can also be used, such as receptor-ligand, enzyme-substrate, etc. The binding of some proteins to a ligand can be made dependent on the presence or absence of a third molecule and thus protein-ligand interactions can be made reversible under moderate conditions of temperature, ionic strength, and pH.

2. Making the Seed Using Optical Tweezers.

The first step is to make the sequence of colloidal particles that will serve as the seed. Holographic optical trapping assembles chains of particles with a random or specific ordering of the unprimed particles. For example, the "word" ABABBA can be formed. The assembly of the beads into a "word" is performed at a temperature above the melting (hybridization) temperature of all hybridizing pairs. After the particles are brought together to form the desired sequence, the temperature is lowered so that the beads link together by hybridization of the U palindrome ("longitudinal" bonding). The beads are then permanently cross-linked by psoralen under UV illumination. This word or sequence serves as the "seed" for self-replication.

A holographic optical trap (HOT or laser tweezers) has the ability to control many particles (up to 1000) in three dimensions. The ability to sculpt light in three dimensions also allows for the creation of linear optical traps in which interacting particles can be captured. If there are gradients that attract the particles to the center of the line trap, then the distance between two particles is a direct measure of the particle interaction. A force distance curve can be obtained by varying the light intensity. An example of the sophistication of the assembly technique is demonstrated below. Such a holographic assembly is used to arrange DNA coated and fluorescently labeled colloidal particles into the chains, planes and more complex structures that will be the seeds for the self-replication process.

It has been previously shown that, for example, 173 colloidal silica spheres can be arranged in a single plane within a three dimensional sample volume. Comparable planar rearrangements also can be implemented with a single rapidly scanned optical tweezer in a time-shared configuration or with the generalized phase contrast method. Unlike these other techniques, however, holographic trapping also can create three-dimensional structures. The holographic trapping system can stack micrometer-scale objects up to seven deep along the optical axis. In addition to arbitrary three-dimensional control, holographic traps offer other advantages for assembling templates for self-replication. HOT patterns can be more extensive than timeshared arrays that must periodically release and retrieve each trapped object. Additionally, the lower peak intensities required for continuously illuminated traps are less damaging to photosensitive samples. More importantly, individual holographic traps' characteristics can be tailored to different objects' optical properties to facilitate optical assembly of disparate materials. Extended holographic tweezers, which sometimes are called "line traps", can be used for measuring interactions between colloidal particles, as discussed below. They differ from point-like optical tweezers by acting as one dimensional potential energy landscapes for trapped objects. In addition to their applications for aligning and assembling small objects, line traps provide the basis for a precise, versatile, and rapid method for measuring colloidal interactions. It has recently been shown that is possible to project line traps with the same holographic trapping apparatus used to create arrays of discrete traps. The technique, called shape-phase holography, provides absolute control over both the intensity and phase profiles of an extended optical trap. Unlike competing techniques, this approach creates traps with optimal axial intensity gradients, which can manipulate objects in three dimensions, away from bounding surfaces that might alter the objects' interactions.

Holographic traps and line traps are also used for measuring the strength of interactions between particles, providing advantages over conventional methods. Interactions relevant for the self-organization of micrometer-scale colloidal particles typically are characterized by length scales ranging from a few nanometers to several micrometers and force scales ranging from several attonewtons to a few piconewtons. Small variations in these interactions can dramatically change a colloidal dispersion's stability against irreversible flocculation, and influence both the kinetics and dynamics of self-assembly. Therefore, accurately characterizing colloidal interactions is an integral part of designing and implementing the rules governing accurate self-replication of colloidal microstructures. In addition to the specific interactions mediated by ligated DNA, functionalized colloidal particles will also interact non-specifically, for example through electrostatic coupling, van der Waals interactions, and through solvent-mediated depletion interactions. These non-specific interactions determine the dispersions' stability and can modify both the strength and temperature dependence of intended specific interactions. Accurately assessing the colloidal pair potential is still more important and substantially more challenging in heterogeneous dispersions, where the interactions between all different pairs of particle types come into play. The innovation of holographic line tweezers and new statistical methods for analyzing trapped particles' motions can cut measurement time from days to minutes without sacrificing accuracy. This approach, moreover, lends itself to measuring interactions between dissimilar particles. This approach to measuring colloidal interactions is easily combined with microfluidic sample handling and external environmental controls. DNA-mediated interactions thus can be measured as a function of temperature and electrolyte composition to arrive at optimal conditions for self-replication. Because this method can provide quantitative results with as few as two particles, interaction measurements can be used as a guide for optimizing particle synthesis and functionalization. In addition to measuring colloidal interactions, optical tweezer measurements will be useful for assessing the mechanical properties of chemically linked assemblies of particles. This information, in turn, will be useful for designing protocols for transferring the organization of an optically assembled template to chemically amplified copies.

3. Temperature and Magnetic Field Protocol for Replicating the Seed.

We now describe the replication process of the word ABABBA. The seed ABABBA is introduced into a bath of particles with a large quantity of the singlets A, A', B, B' present. The bath is above the melting temperature of all hybridized pairs. A weak magnetic field is applied which aligns the ABABBA seed parallel to the field. The temperature is lowered to the melting temperature for particles with one transverse bond (between a primed and its unprimed counterpart on the seed), two longitudinal bonds (between its two primed nearest neighbors), and three magnetic dipole interactions (see FIG. 6). At this temperature the complementary word A'B'A'B'B'A' assembles alongside the seed and anneals, to rid the system of defects. The two chains remain aligned along the field direction. After annealing, the system is exposed to UV light which cross-links the palindromes thereby permanently fixing the daughter A'B'A'B'B'A' sequence. The temperature is then increased above all melting and hybridization temperatures. Then, as shown in FIG. 6, the A'B'A'B'B'A' strand separates from the seed ABABBA forming a replica.

The process of temperature change and UV exposure is then repeated cyclically. In each cycle the original and daughter cells are replicated doubling the population. This leads to an exponential population growth as long as the supply of lettered particles persists.

In order to readily identify these particles under an optical microscope, these particles can also be distinguished by the fluorescent dyes they contain: a red dye for the A and A' particles and a green dye for the B and B' particles.

4. Hairpins in DNA Palindromes

Figure 7:
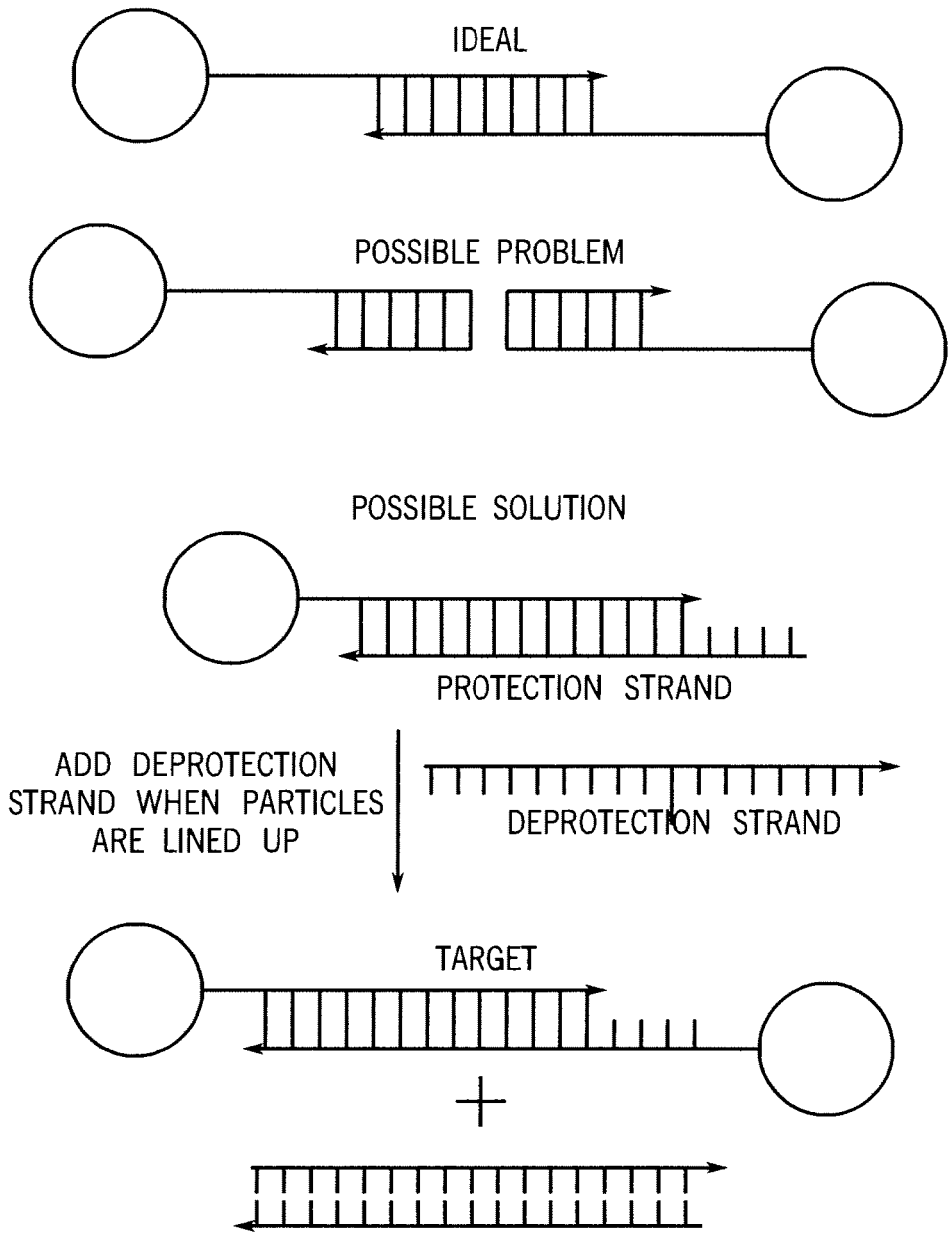
FIG. 7 illustrates how palindromic DNA ends can self-anneal, rather than annealing with a palindrome on another particle. One solution is to provide a "protection strand" that prevents self-annealing. Once the particles have aligned in a daughter, a deprotection strand is added, removing the protection strand, and allowing annealing between strands on adjacent particles.

Specific DNA-DNA interactions can be determined by any two complementary sequences. The number of required complementary sequences can be reduced by the use of palindromic (self-complementary) sequences, which allow any particle to bind to any other particle. A possible problem is that palindromic DNA, at low concentration, and particularly when isolated, can form hairpins, since its 5' end can pair with its 3' end. This would render the DNA sequence non-reactive. One way to defend against such an eventuality is to protect the sequence. FIG. 7 illustrates protection of the ends. The drawing has three parts. Illustrated at the top is the ideal interaction. However, the possible problem of forming hairpins is illustrated below it, preventing interaction. A possible solution is shown at the bottom. The palindrome is flanked on one end by the extra sequence, drawn in green, so that it would compete favorably with the hairpin phenomenon, particularly at high local concentration. A protection strand is added (at high enough temperature to overcome any hairpins already present), preserving the system for alignment. When the particles are aligned, a deprotection strand is added according to the technique of Yurke et al. "A DNA-fuelled molecular machine made of DNA" Nature 406: 605-608 (2000). It will remove the protection strand because it has an extra portion (drawn blue) that acts as a toehold for it to bind to the protection strand and then to branch migrate it off the binding strand. The extra length of this duplex acts as a thermodynamic trap. The particles are then free to bind to each other.

Other solutions to hairpin formation including changing the pH, temperature or other factors, to be unsuitable for hairpin formation until the particles are in place. This approach is explored in greater detail in FIGS. 23-27.

5. Mis-Pairings of Primed and Unprimed Particles

Mispairings may also occur. FIG. 28, for example, shows an A' particle heading into its intended position to across from an A particle on a parent strand (seed) and between two A particles in a daughter strand. The B' particle makes bonds with its neighbors and is clearly in its lowest energy state. Thus, the arrangement of particles would be disrupted, resulting in a permanent error in the daughter strand that would propagate in subsequent generations. While such errors might be interesting for evolutionary studies, they might also significantly compromise the amplification process.

One solution to this problem is to adjust the length of the Watson-Crick pairings for the U-U and P-P strands compared to the A'-A and B'-B strands such that the melting temperature of the U-U and P-P strands is several degrees lower than that of the A'-A and B'-B strands. Then, in the first stage of the copying process, the temperature would be lowered below the melting temperature of the A'-A and B'-B strands, but kept above the melting temperature of the U-U and P-P strands. This would allow the copying process to proceed without interference from the longitudinal bonds. Once the primed-unprimed parings between the parent and daughter strands are made, the temperature would be lowered, allowing the unprimed longitudinal pairings to occur. Exposure to UV light would then make the longitudinal pairings permanent, as before.

6. Structural Control of DNA

One basic scheme for self-replication is that based on the specific and reversible hybridization interaction of complementary Watson-Crick DNA pairs. The arrangement of bases on the single stranded "sticky end" of a DNA chain is at the heart of the strength, specificity, efficiency, and robustness of the interactions that will bind our colloidal particles. DNA sequences may be designed to produce sticky ends and many more complex structures. Work since the 1980's has shown that DNA can be used to form DNA objects and nanomechanical devices from components that are closely related to the branched DNA Holliday intermediate in genetic recombination. It is easy to design synthetic DNA molecules that self-assemble to produce stable branches. It has been that the structure of DNA in the vicinity of sticky ends is classical B-DNA (the Watson-Crick structure), so it is possible to know the detailed geometry of local product structures at the point of cohesion. Thus, if we know where the atoms are on one side of a sticky end, we know where they are on the other side. This is a key step towards making the connection between the microscopic and the macroscopic: predictable geometry enables one to program structural features on the nanometer scale.

Figure 8:
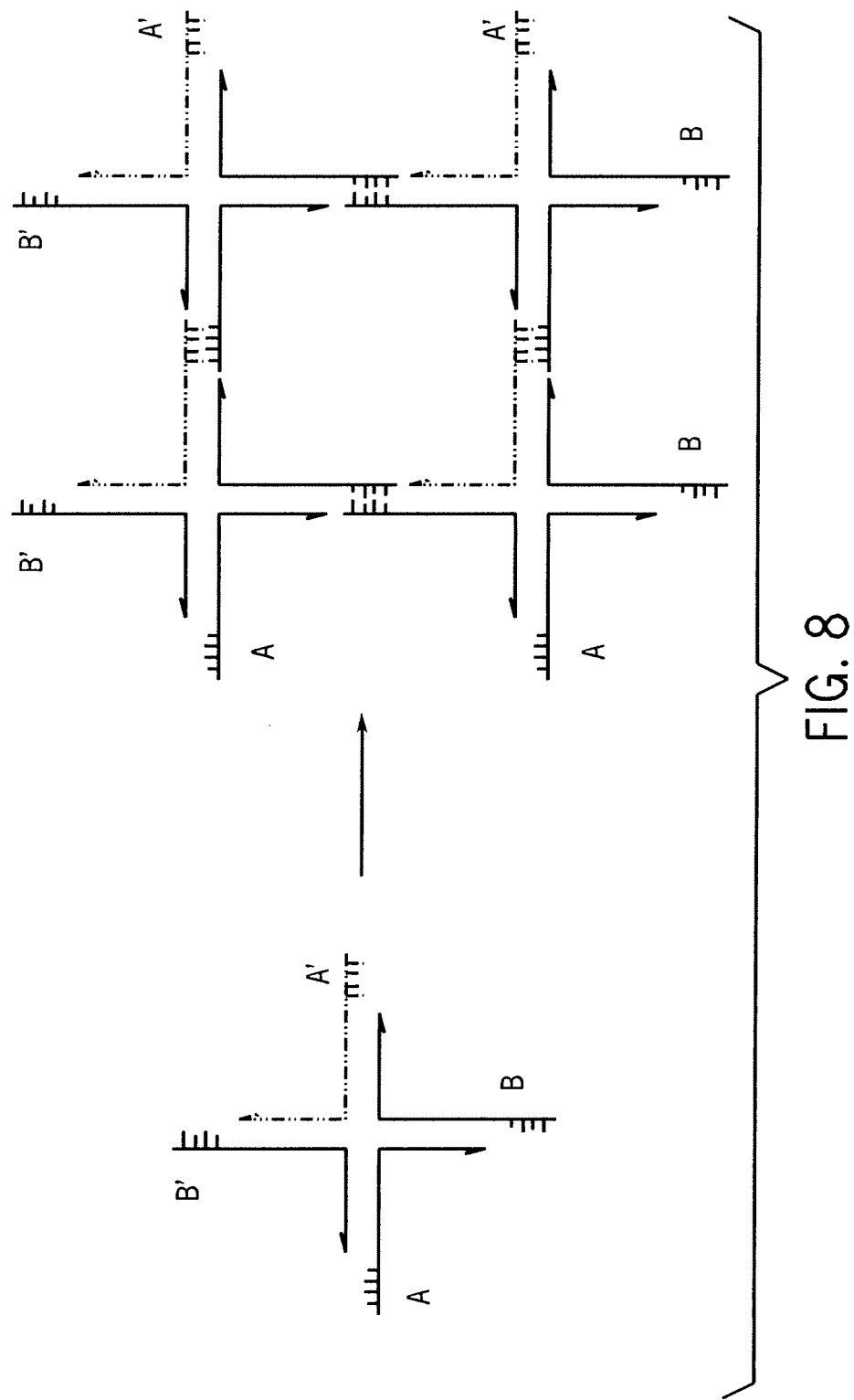
FIG. 8 illustrates how DNA can self assemble to form a quadrilateral. Four DNA branched junctions with sticky ends self-assemble to form a quadrilateral. The sticky ends on the outside allow larger assemblies, so that one can form a 2-dimensional periodic array from the motif.

Using sticky ends to control the interactions of branched DNA molecules, enables us to construct N-connected objects and networks. For example, in FIG. 8, a DNA branched junction molecule with sticky ends self-assembles to form a quadrilateral. Using this notion, it has been shown how to build stick polyhedra with the connectivities of a DNA cube, and a DNA truncated octahedron, where the edges are double helical DNA, and the branch points of junctions correspond to the vertices. The conventional branched junction is fairly flexible. Stronger, more rigid structures can be made with the antiparallel DNA double crossover (DX) molecule, that contains two laterally fused helices is about twice as stiff as conventional DNA. The fusion between helices is achieved by crossover of strands between the helices.

Figure 9A:
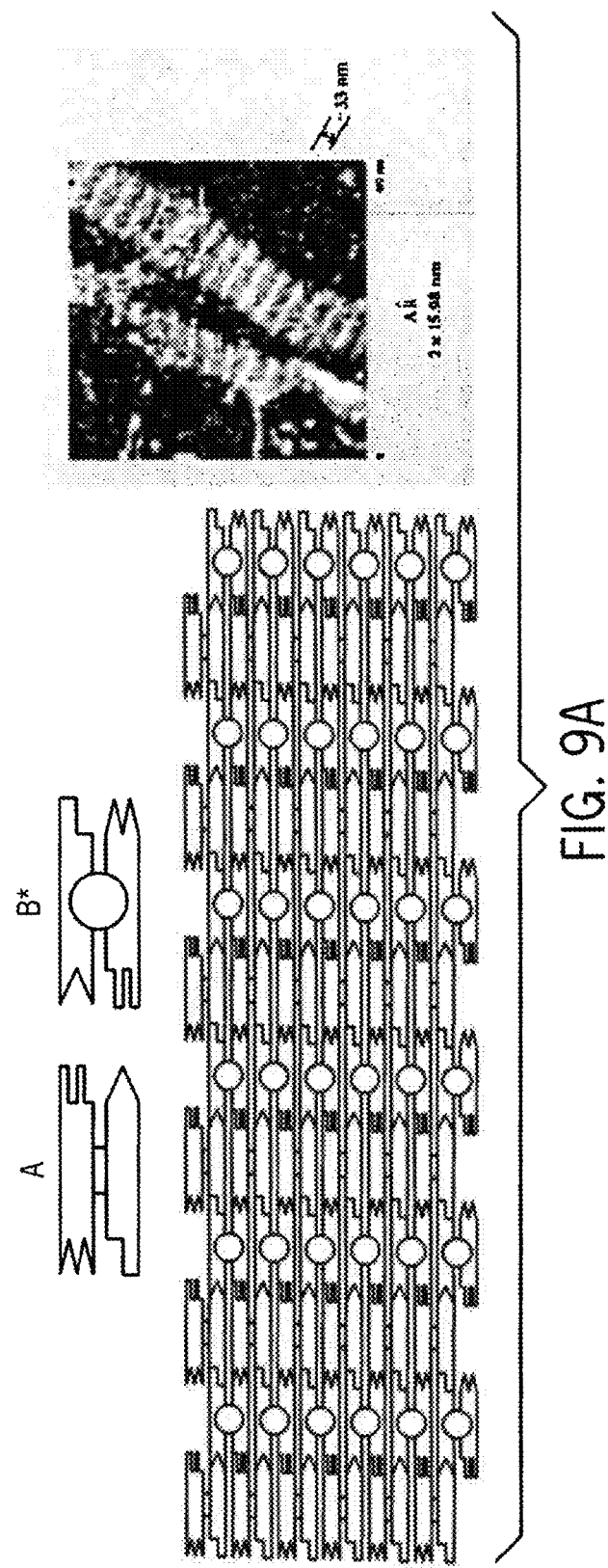
FIG. 9 illustrates how stiffer antiparallel DNA double crossover (DX) molecule, with two laterally fused helices can be used to form 2D periodic assemblies, via self assembly. 9(a) and (b) shows a schematic and actual Atomic Force Microscope Image of 4×16 nm DX tiles that contain a protruding feature yielding striped patterns of predicted separations of 32 nm (a) and 64 nm (b). 9(c) is a TX (antiparallel triple helix) containing a rotated tile the sticks out on both sides. 9(d) is a DNA parallelogram with 13×20 cavities.
Figure 9B:
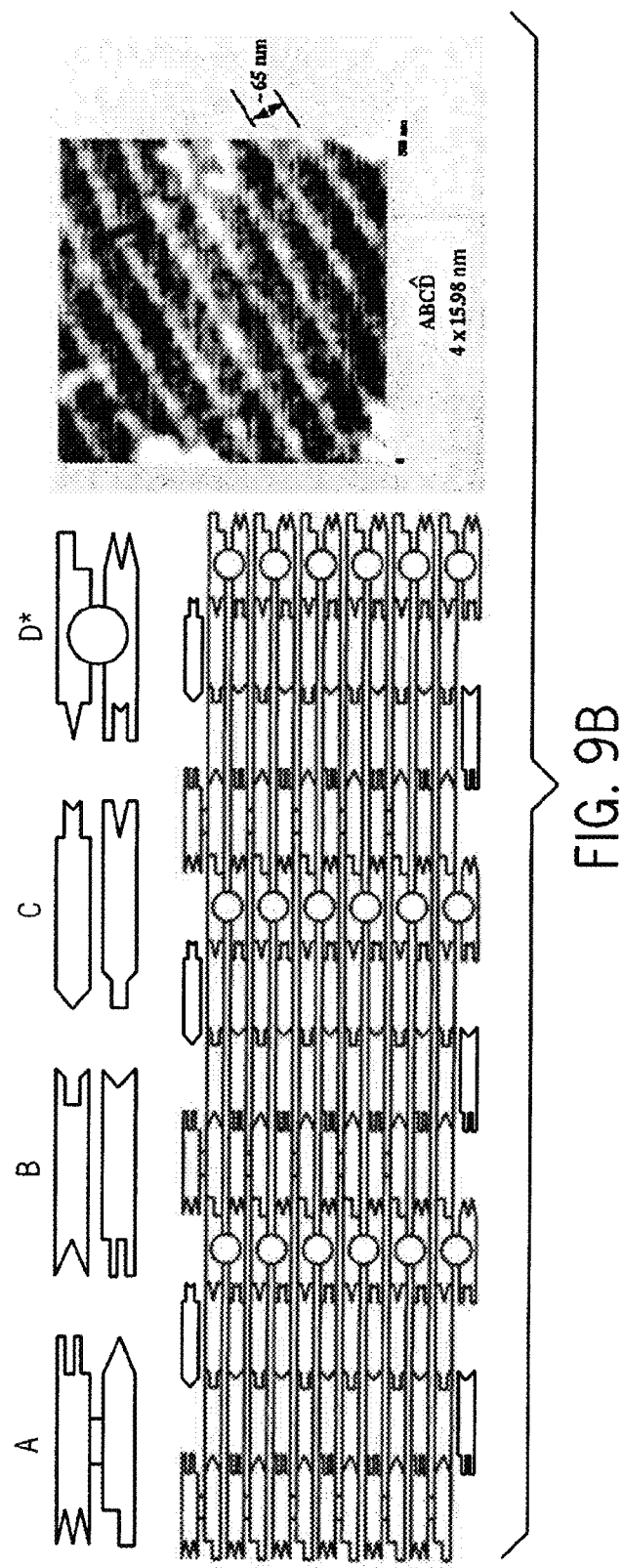
Figure 9C:
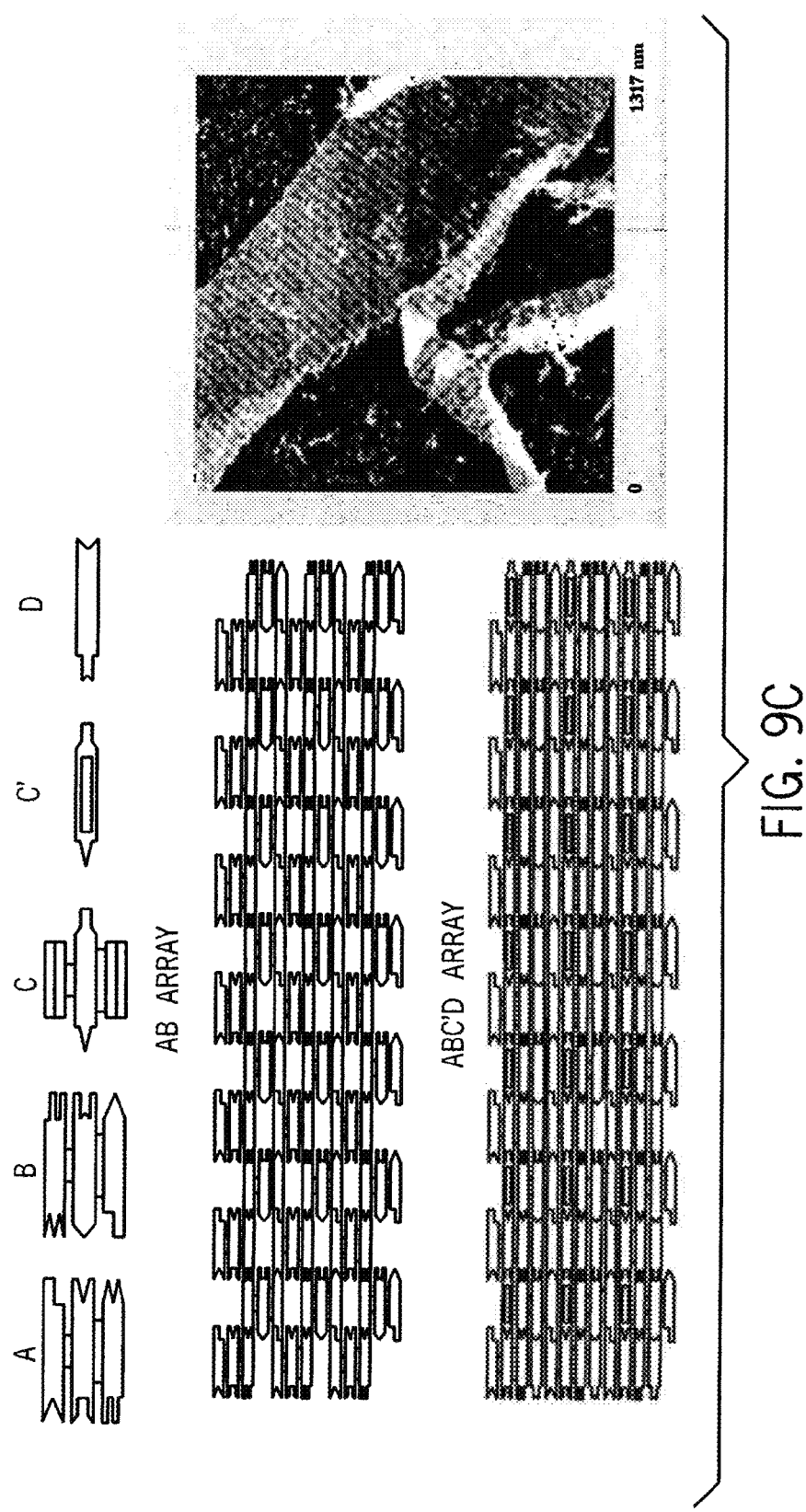

DX molecules can be used to form 2D periodic assemblies, via self assembly, as shown in FIG. 9. Triple-crossover (TX) molecules and DNA-parallelograms can also be used to form 2D periodic assemblies. DNA motifs used for filling 2D or 3D space as tiles. DNA-based nanomechanical devices have also been developed, such as the sequence-dependent PX-JX$_2$ device, and a bipedal walker.

Figure 11:
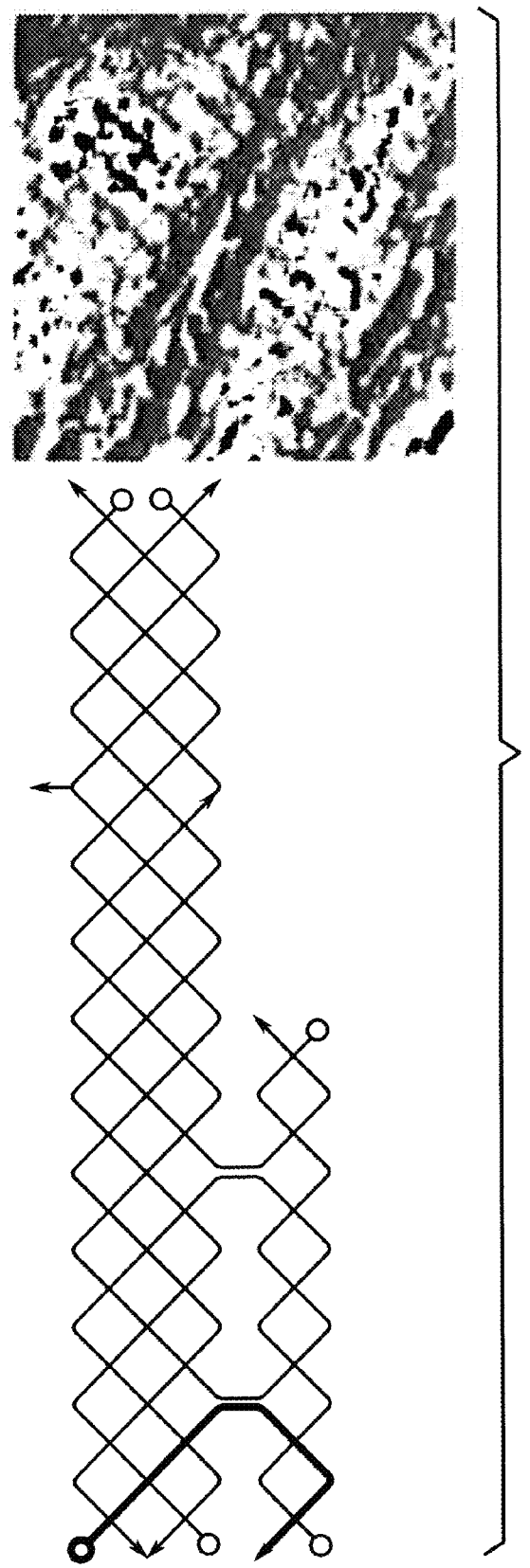
FIG. 11 shows a cassette to insert the PX-JX2 device into a 2D TX array. The device is shown on the right side of the schematic in the PX conformation. The lower domain on the left inserts into a gap (19) in a 2D array. This is confirmed by the AFM image at the right.

The nanomechanical device machine cycle is shown in FIG. 10*a*. The structure on the left (PX) has wrapped itself a half-turn more than the structure on the right (JX$_2$). The green strands at the center of the PX molecule are removed by techniques described by Yurke et al., and the yellow strands can be added, to switch between states. FIG. 10*b* shows that this device controls the relative orientations of DNA trapezoids, a motion that is detectable by the AFM. In a key development, we have now made a cassette that allows the insertion of this device perpendicularly into a 2D) array, as shown in FIG. 11. This motion is also detectable by AFM.

The development of this cassette will enable us to couple devices with arrays, and will lead to the development of nanorobotics, independently moving devices at fixed places in space.

Figure 12A:
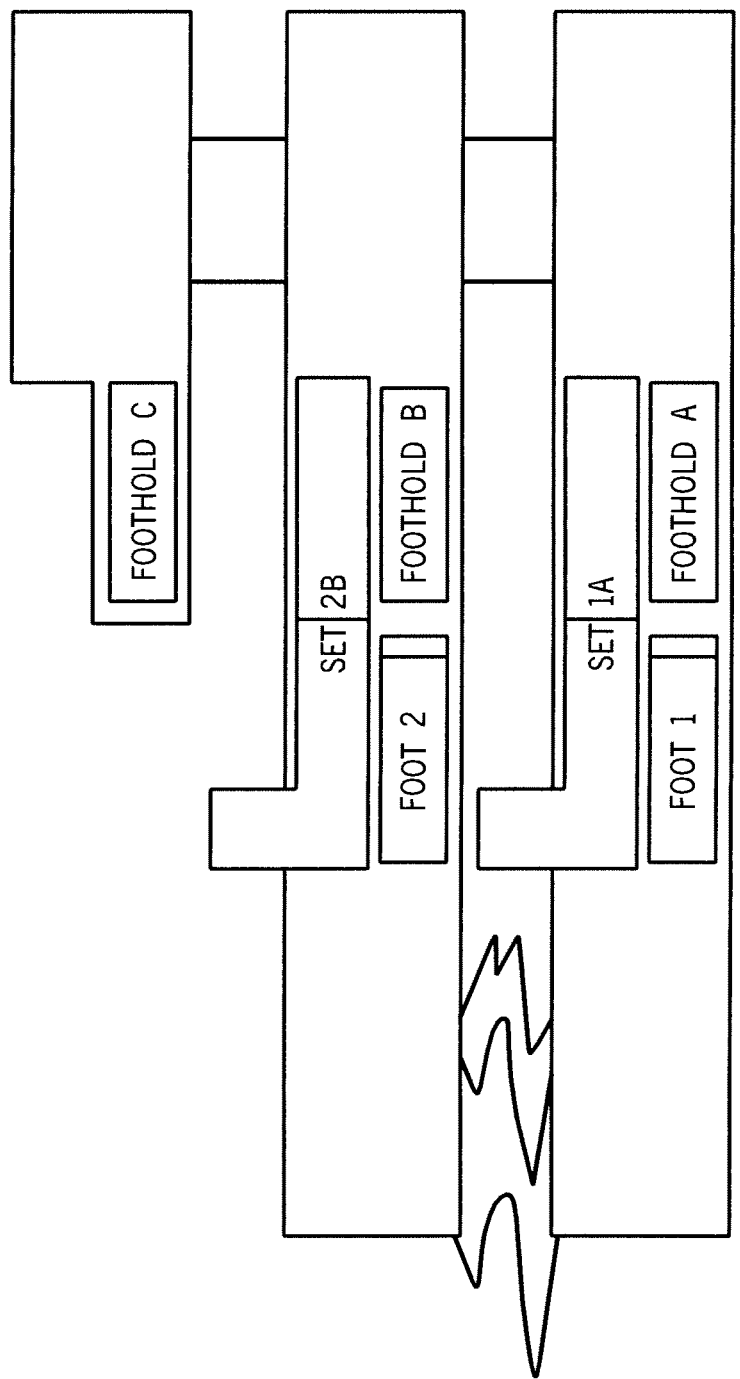
FIGS. 12a and 12b show a nanomechanical walking device constructed from DNA, constructed of two double helical domains held together by three loose strands. It is held to a track by two set strands. Removal and replacement of the set strands displaces the top domain to the top of the track and the bottom domain to the middle.
Figure 12B:
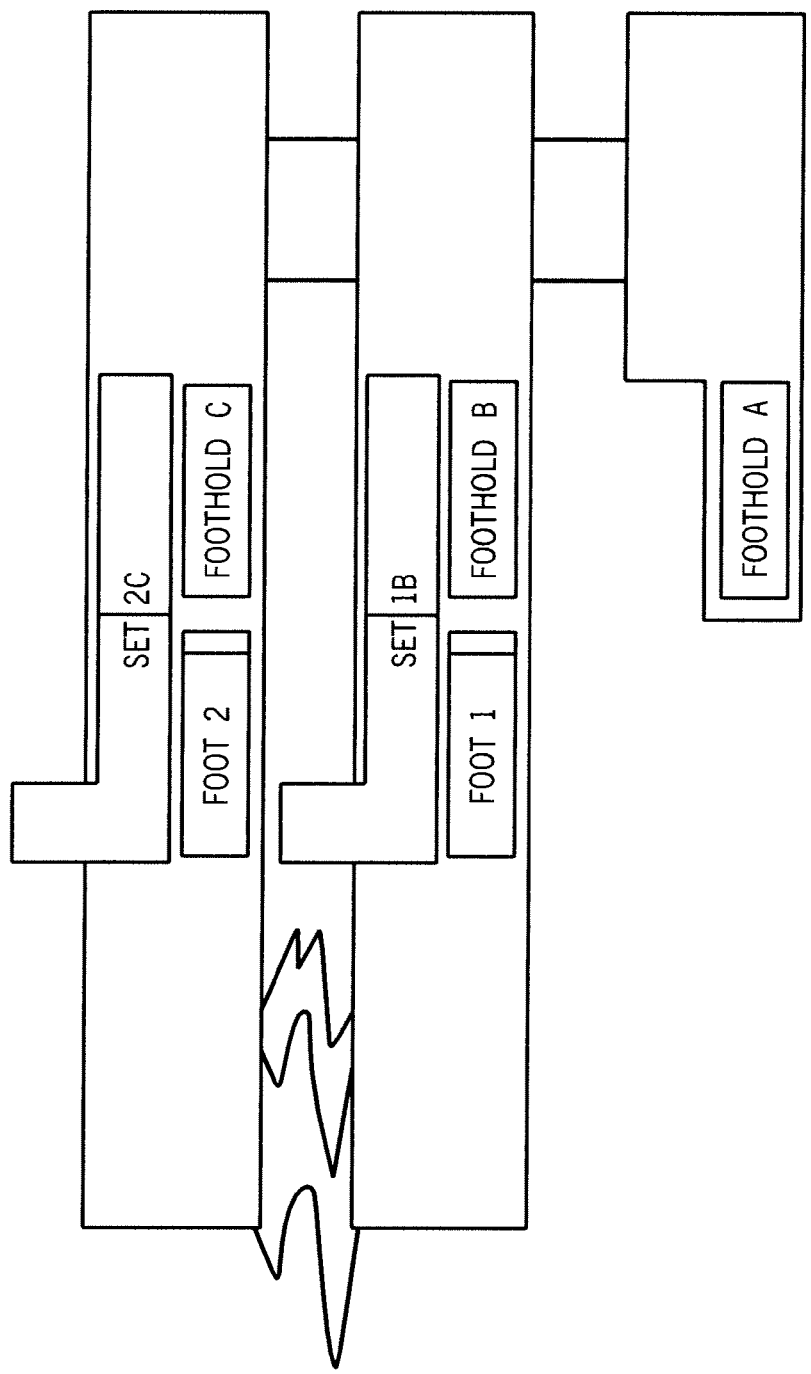

Another device known in the art is a biped designed to walk on a track, as shown in FIG. 12, originally described in Sherman and Seeman, "A precisely controlled DNA bipedal walking device" *NanoLetters* 4: 1203-1207 (2004). The device is based on the notion that one can move each of its parts individually. Thus, the top domain of the ochre device is released from the blue track by removal of the set strand holding it there, and then addition of a new set strand enables it to latch on to the top domain. The flexible strands holding the two domains together enable it to stretch that distance. The bottom domain is moved to the middle domain in the same way.

7. Colloidal Interactions Using DNA-Coated Particles

Previous researchers had shown that specific aggregation of DNA-coated particles was possible and that some degree of reversibility could be achieved, but to be useful in a materials sense, much more control is required. The largest problem was that complementary particles would not separate when heated above the DNA melting temperature. Another force, probably van der Waals at small separations, held them together. The solution was to use a polymer brush to keep the particles out of the range of the van der Waals well while still within range of the DNA attraction.

Figure 13:
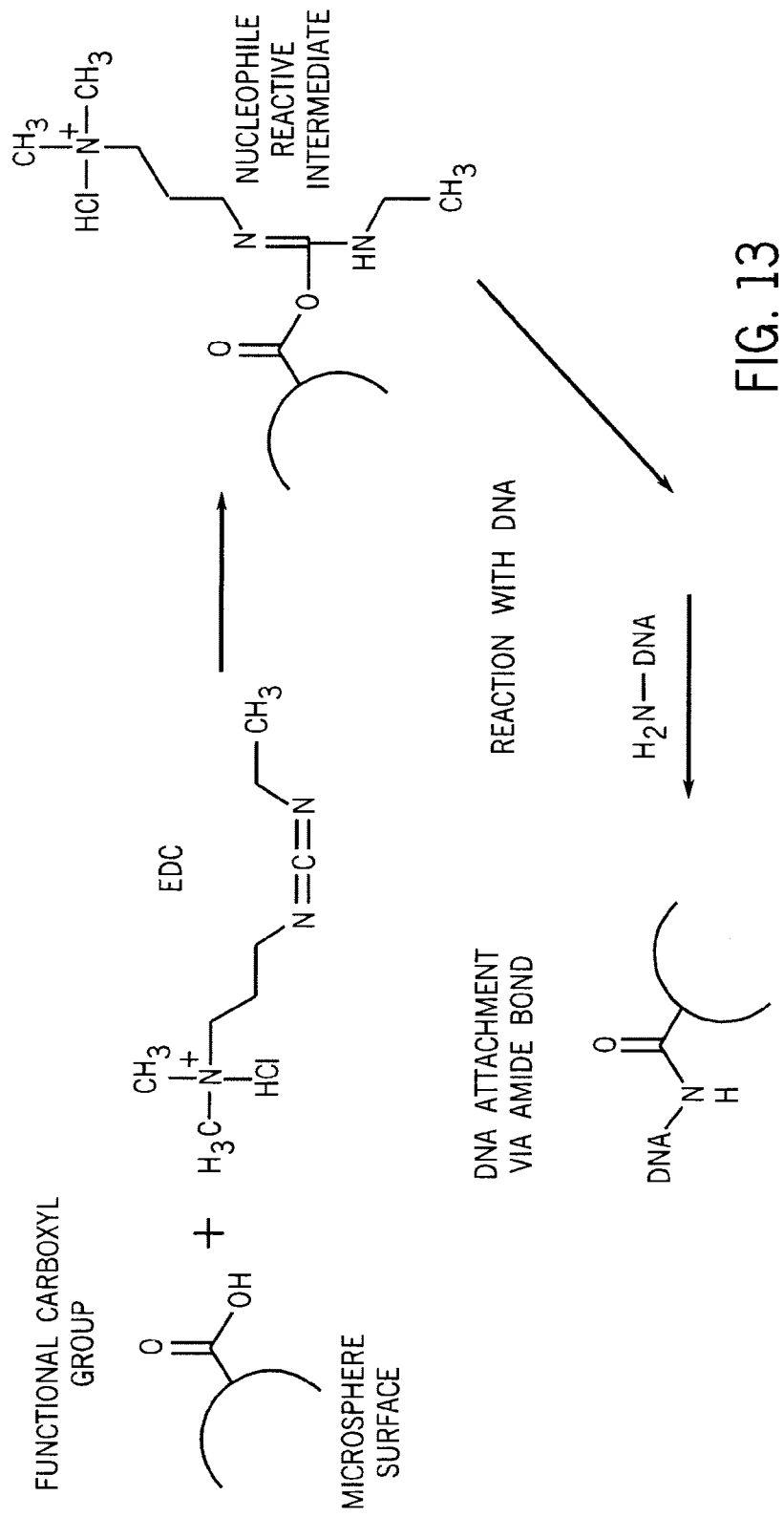
FIG. 13 show a mechanism for attaching amino-modified DNA strands to carboxyl-functionalized microspheres.
Figure 14:
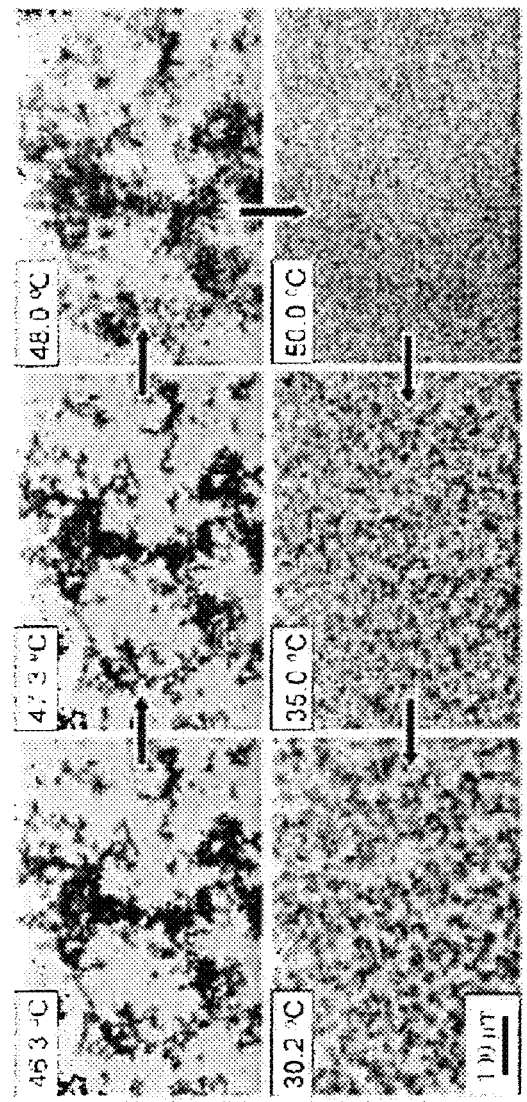
FIG. 14 shows dissociation and aggregation of a two component aggregate at 70 mM Na+. Top left: the beginning aggregate below dissociation temperature. Following the arrows, the sample is heated above the dissociation temperature (47.3 C) and allowed to cool.
Figure 15:
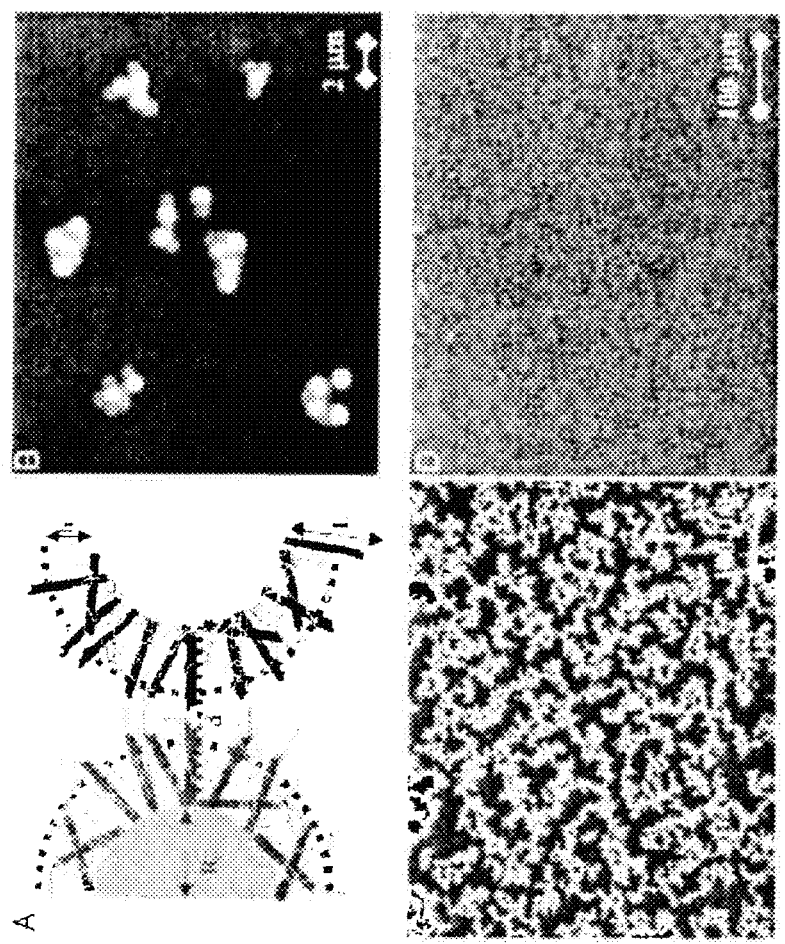
FIG. 15. Specific and reversible aggregation. (A). Microbead surfaces grafted with oligonucleotides. A polymer brush imparts a steric repulsion between the particles and reduces the number of links that may form between them. Part of the DNA end is hidden in this layer of thickness h (B) Specific aggregation. Green beads are specifically linked to red, R-type beads as shown by fluorescent microscopy. (c) 23 C, reversible aggregation observed by means of bright field microscopy of particles stabilized in F108 solution observed 8 hours after mixing G and R beads (D) After raising the temperature to 50 C, the beads completely redisperse.
Figure 16:
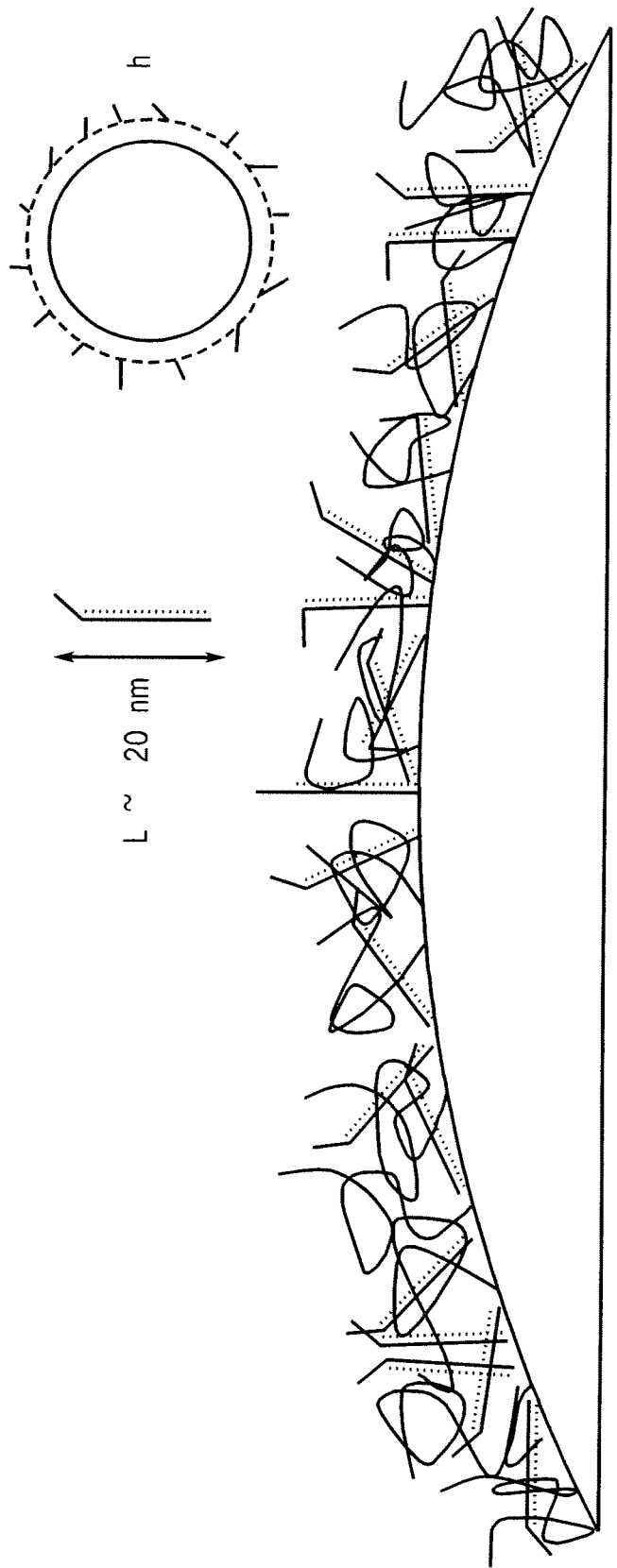
FIG. 16 represents the surface of a colloid bead to which is attached the DNA linker and a variety of polymer brushes to stabilize the interaction with other particles.

FIG. 13 shows one approach to modify the surface of a colloidal particle to accommodate a polymer spacer, PEG, and the DNA sticky end. The images in FIG. 14 show the aggregation of the colloids below the DNA melting temperature, the redispersal hence reversibility on heating and reaggregation on recooling. Another approach is to use a commercial particle with biotin-streptavidin links to attach the DNA and a separate absorbed polymer brush to prevent van der Waals interactions. A length of double stranded DNA is used to keep the sticky end more distant from the particle, and away from van der Waals forces. One of ordinary skill can, of course, adjust the length of the DNA spacer and the size of the polymer brush to control the degree to which sticky ends are accessible by other sticky ends. A schematic of the particles is shown in FIG. 15. Here the complementary particles are dyed with rhodamine and fluorescene to fluoresce red or green. We see the specific association in that there are no direct red-red or green-green pairs. Aggregates only form from red-green bonds. The lower pictures also show the reversibility as redispersal on heating. FIG. 16 represents the surface of a colloid bead to which is attached the DNA linker and a variety of polymer brushes to stabilize the interaction with other particles.

Figure 17:
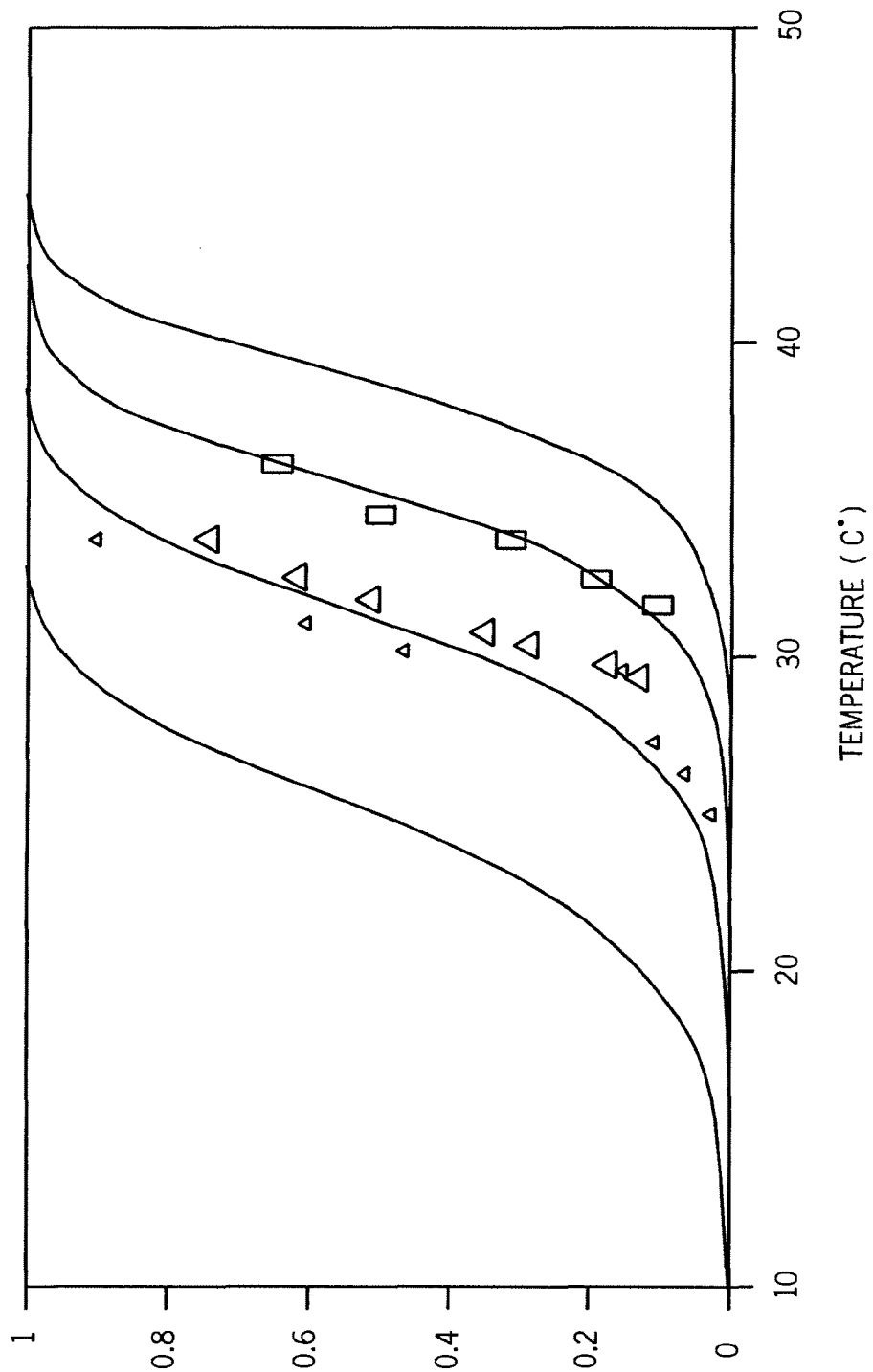
FIG. 17 Fraction of single unbound beads vs. temperature. Discrete marks are the experimental data plotted for four different stabilizers.

A process for self-replication requires control over the DNA melting temperature. This can be done separately by the length and sequence of the DNA sticky ends, but it also can be done by adjusting the adsorbed polymer. A set of melting curves, for different adsorbed polymers is shown in FIG. 17. This figure also illustrates that it is possible to take quantitative thermodynamic measurements by use of confocal microscopy and imaging, and control physical parameters (such as temperature and temperature gradients).

Figure 18:
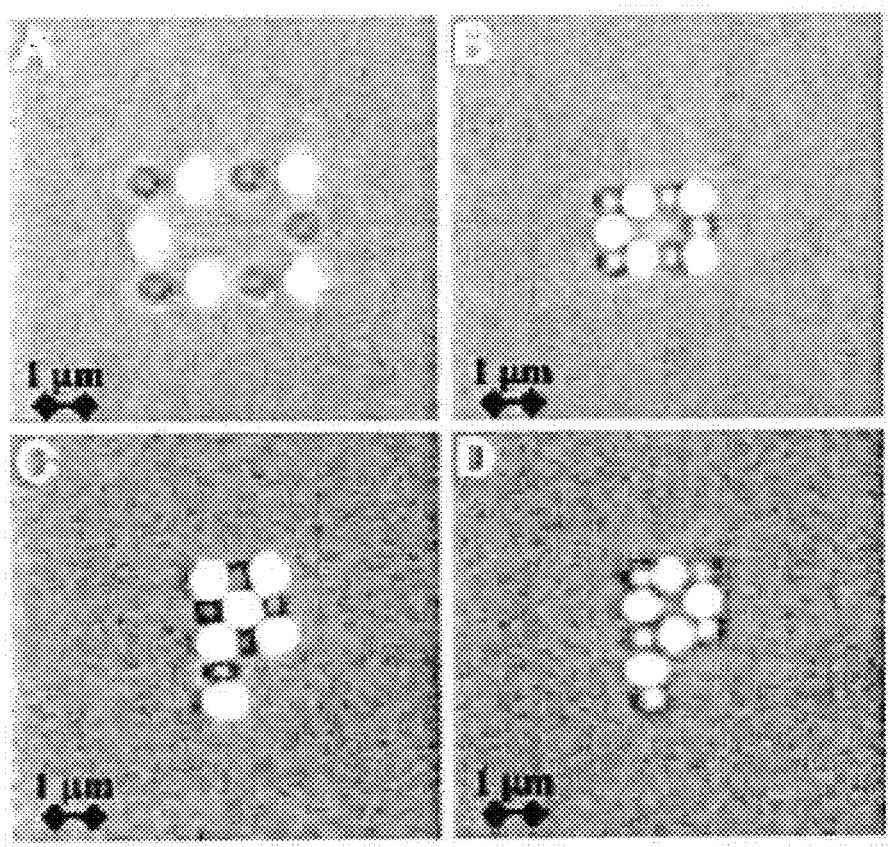
FIG. 18 Directed assembly of particles. Flourescent and nonflourescent particles bear complementary strands of DNA. (A) Particles are first captured in discrete time-shared traps induced by laser tweezers (B-D) Particles are moved in contact to promote hybridization between the DNA strands and for the following rigid structures: a rectangle (B), a full P (C), and an empty P (D).

The fact that we can fabricate seeds by particle manipulation using optical tweezers is illustrated in FIG. 18 where DNA coated particles are positioned, brought together and bound into a few patterns.

8. Colloidal Clusters and Patchy Particles

Figure 19:
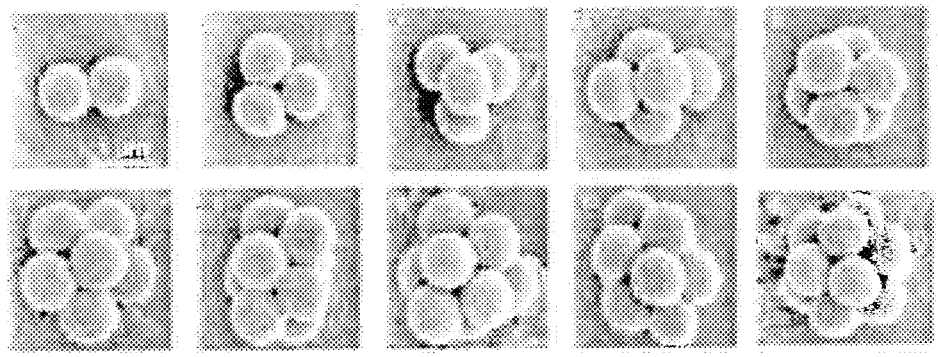
FIG. 19 shows clusters ranging in size from 2 to 11 spheres, in various shapes.

"Colloidal molecules" or "colloidal clusters" refers to any one of a variety of clusters made from colloidal spheres irreversibly linked together at one or more points; these clusters have well-defined shapes and include dumbbells (dimers), triangles (trimers), tetrahedra (tetramers), and octahedra (hexamers), as well as many more exotic clusters. FIG. 19 shows clusters ranging in size from 2 to 11 spheres. With the techniques developed in Pine's group, it is straightforward to produce more than a billion clusters of a given number per batch. See, e.g. Cho et al. "Self-organization of bidisperse colloids in water droplets," *J. Am. Chem. Soc.* 127: 15968-15975 (2005).

Figure 20:
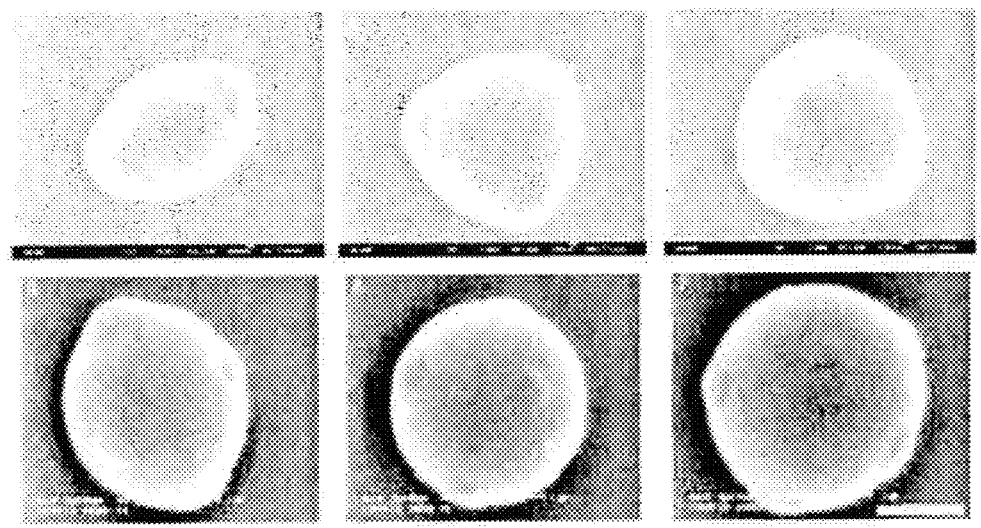
FIG. 20 Colloidal atoms. SEM images of colloidal atoms with symmetrically-placed patches on their surfaces. The number of patches n is indicated in the upper left corner of each image. The number of patches corresponds to the number of spheres that served as seeds for making these particles (as shown in FIG. 19). The scale bar in the lower right hand corner of the n=7 is 1 μm.

The second class of particles are made from the colloidal clusters and consist of particles that are nearly spherical but have a finite number of small chemically distinct patches on their surface. SEM photographs of particles with 2-7 patches are shown in FIG. 20.

These patches can serve as centers for creating bonds along well-defined directions to other colloidal particles, much as atoms do; we call these particles "patchy particles" or alternatively "colloidal atoms." Like conventional atoms and molecules, each of the colloidal atoms and molecules possess well-defined symmetries: for a given number of particles or patches n, all colloidal molecules are identical, as are all colloidal atoms of a given n. The middle patchy particle in the bottom row is especially interesting in the present context. It has 6 patches. Thus, if we assembled a string of such particles in a straight line and connected them to each other by opposing patches, which would leave four exposed patches on each particle along the string where other particles could attach laterally.

9. Industrial Applications

Success in creating a self-replicating system with polystyrene beads can be translated to a wide range of materials, such as metals and ceramics, semiconductors and plastics. Such composite, microscopically-designed, materials should find wide application as sensors, solar cells, battery and fuel cell components, as well as new materials for personal products and pharmaceuticals.

Figure 21:
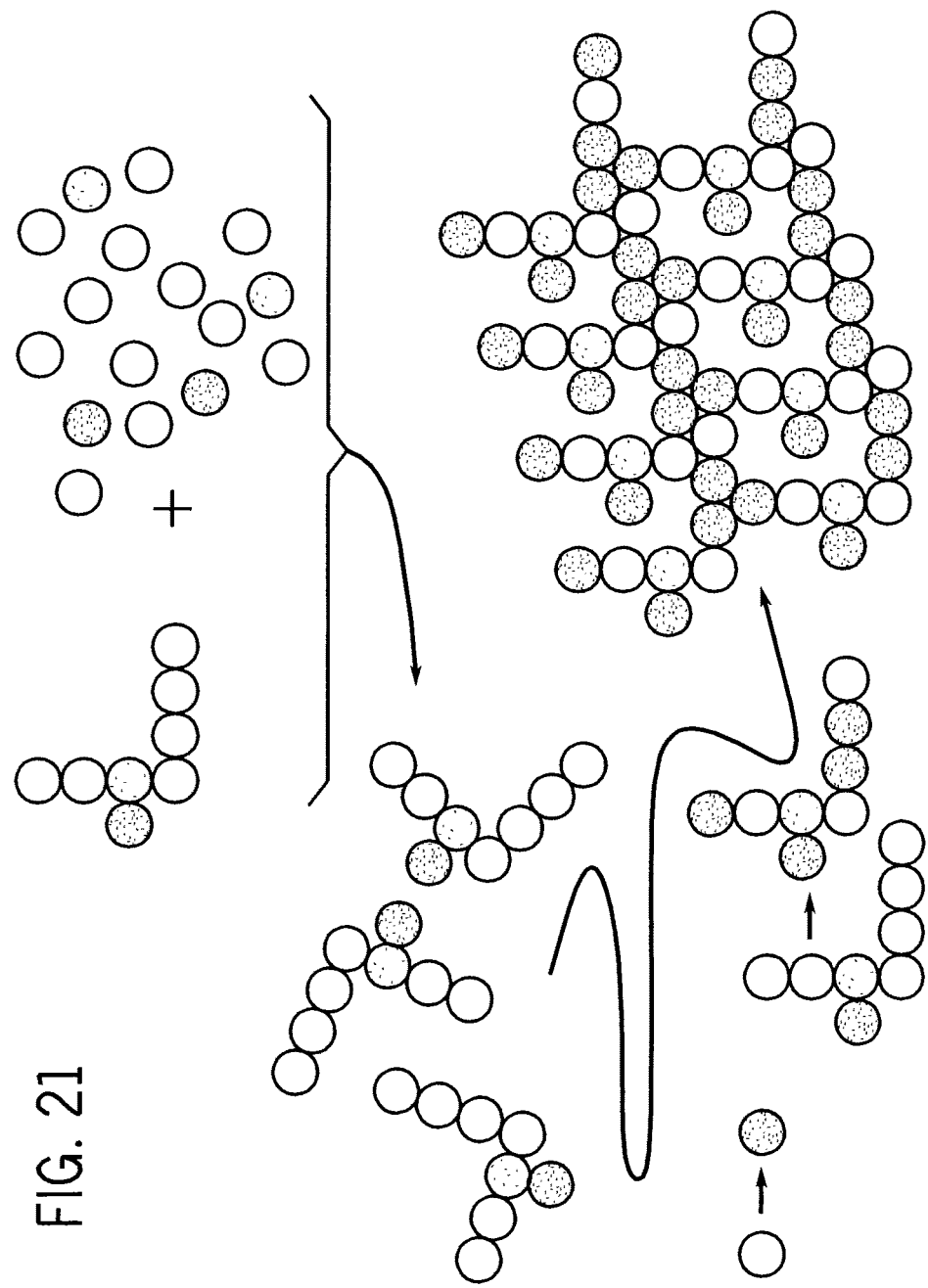
FIG. 21 shows how a photonic crystal can be built by replicative assembly from a specifically constructed seed comprising structural elements, a fluorophore and photoactive quencher.
Figure 22:
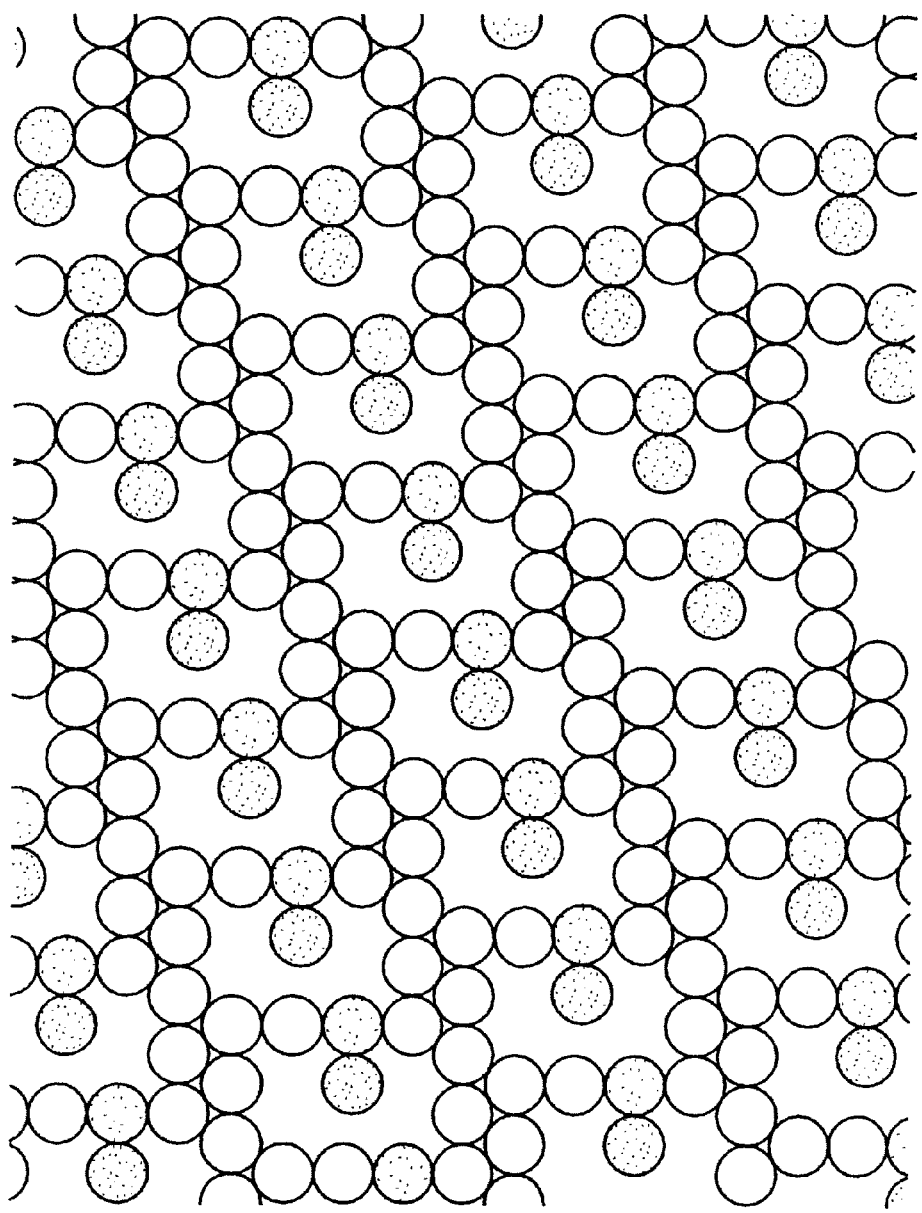
FIG. 22 shows the resulting photonic crystal, in which the spacing of fluorophores and quenchers in space can be strictly controlled. Current techniques of crystal manufacture lack this control, and fluorophores and quenchers are distributed randomly.

FIG. 21 shows how a photonic crystal can be built by replicative assembly from a specifically constructed seed comprising structural elements, a fluorophore and photoactive quencher. FIG. 22 shows the resulting photonic crystal, in which the spacing of fluorophores and quenchers in space can be strictly controlled. Current techniques of crystal manufacture lack this control, and fluorophores and quenchers are distributed randomly.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The following non-limiting Examples are illustrative of various aspects of the invention.

Example I

Demonstration of Self-Replication of a Non-Biological System

An easily identifiable single seed of fluorescently is labeled red A and green B type spheres, and is permanently linked in a sequence, say ABABBA. The seed is introduced to a system of stock A, B, A' and B' spheres and cycle the physical and chemical environment, causing a new complementary sequence A'B'A'B'B'A' of colloidal spheres to form. After one cycle a duplicate is observed, after two cycles four copies, and after N cycles $2^N$ copies. Observation of another seed, say AAAABBAAA, and exponential growth, demonstrates self-replication.

Figure 23:
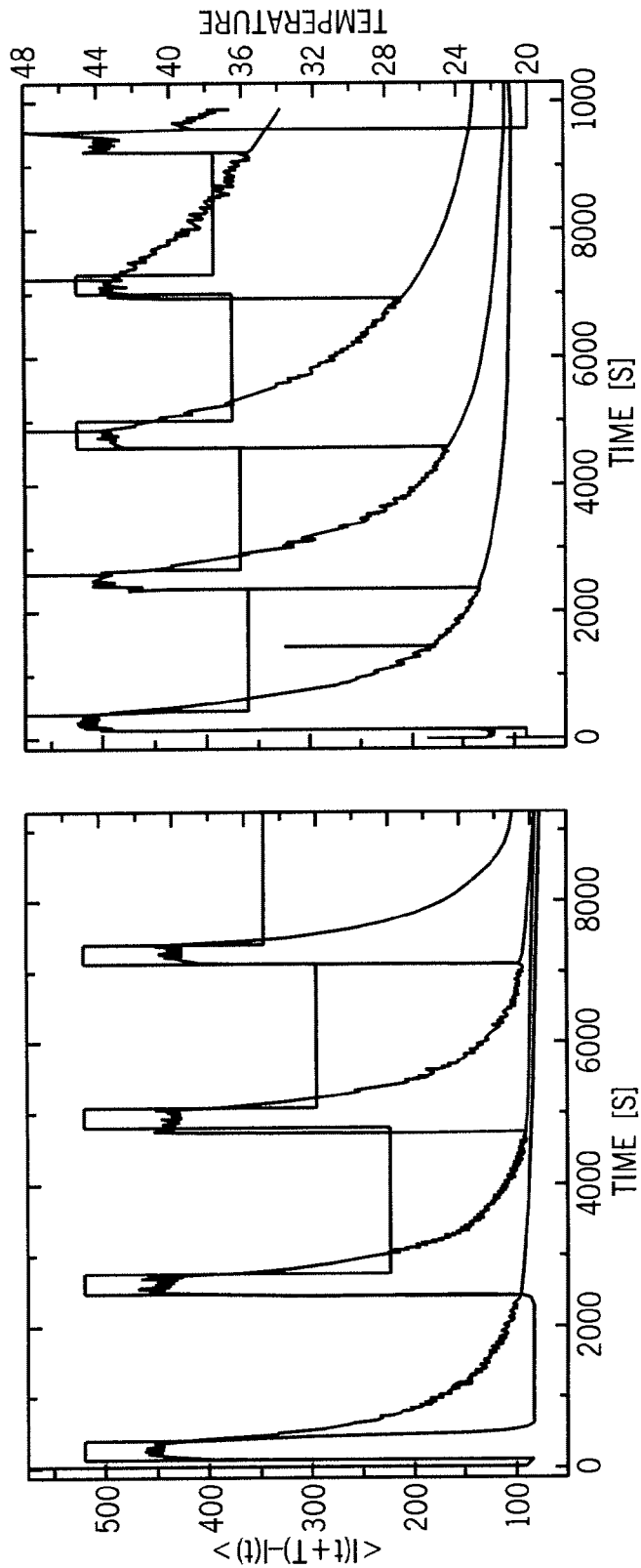
FIG. 23 shows the kinetics of particle aggregation over time at different temperatures.

Control of particle interactions is an important factor. The temperature at which complementary strands of DNA anneal and which they melt is typically for a large population of DNA (i.e. the average temperature of annealing and melting). For small amounts of DNA on particles, particle association and dissociation may occur at different temperatures, in part due to kinetics. Seee Crocker *Proc. Natl Acad Sci USA* 102: 4225 (2005). FIG. 23 shows the kinetics of aggregation of DNA-coated beads as a function of temperature and time. A pool of particles was cycled through temperatures up to 44 C (the melting temperature), and then rapidly cooled. When rapidly cooled many centigrade below the melting temperature, aggregates formed that survived until the temperature was raised to 44 C. The difference between the temperature at which the beads are allowed to aggregate is progressively raised. The left hand side shows that aggregates will reversibly form and then dissociate, through changes in temperature, when the temperature is sufficiently different from the melting temperature. However, as shown in the right hand side, as the aggregation temperature approaches the temperature of melting, the aggregation kinetics are inhibited and many aggregates to not form. This information is important for determining the temperature at which aggregates form. The reverse process is useful for demonstrating the temperature at which aggregates will dissociate.

Figure 24:
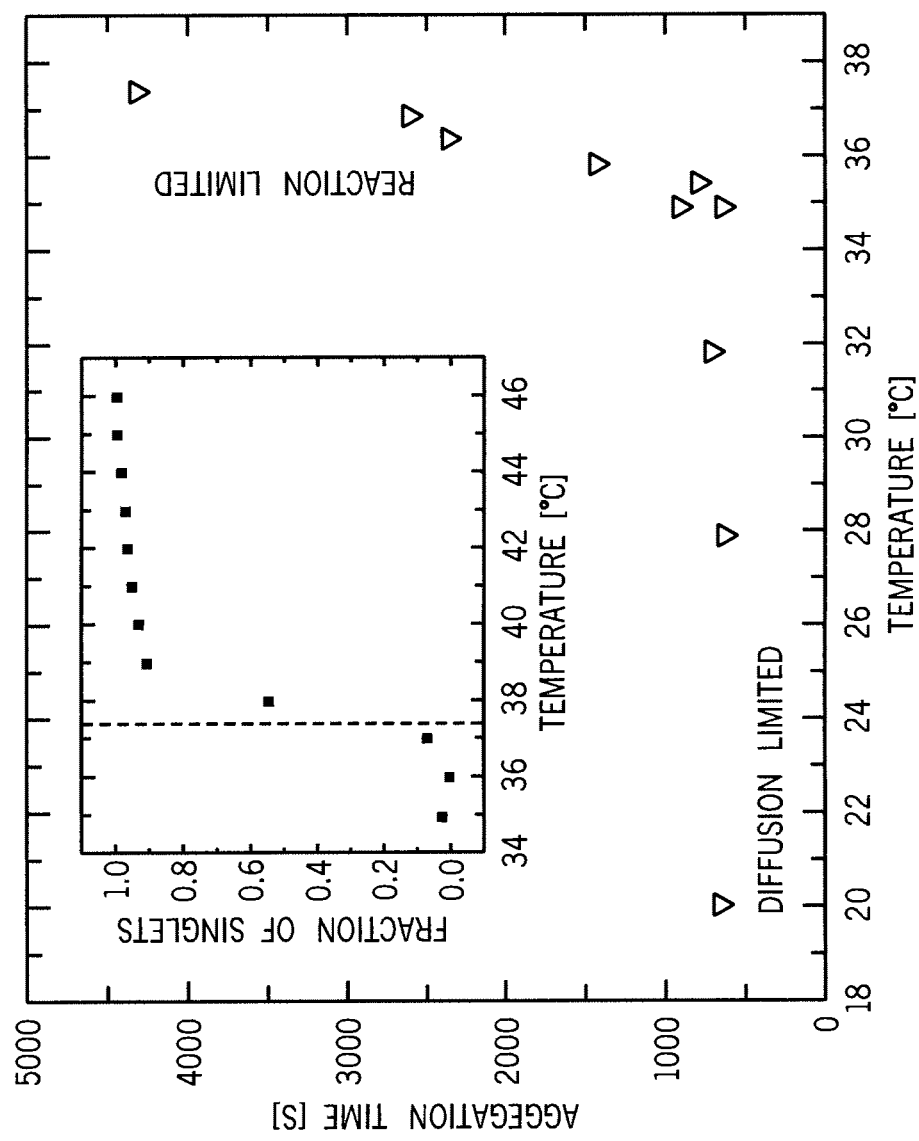
FIG. 24 shows the effect kinetics of particle aggregation over temperature.

FIG. 24 shows the effect kinetics of particle aggregation over temperature. The aggregation temperature and melting temperatures, and their difference, is important for controlling the association and dissociation of particles. If the two temperatures are close (a low "width") then small changes in temperature can be used to reversibly control particle-particle interactions.

A particle with palindromic ends can bind to any other particle with the same palindromic ends. Thus, the number of sticky ends required to facilitate particle-particle interactions is lessened, compared to what would be required if non-palindromic ends are used. The downside, however, is that palindromic DNA can self hybridize, forming hairpins. It can also hybridize with adjacent molecules of the same DNA in the same molecule (intraparticle bonding), which competes with interparticle bonding. (FIG. 26). Palindromic interactions can be minimized by the use of protection strands (Yurke techniques), however, the use of protection strands creates extra complexity to any synthetic process. Alternative approaches to control disfavored palindrome DNA interactions are explored in experiments which are illustrated in the following figures.

For a palindrome to form a hairpin, the DNA must bend in on itself. Similarly, for DNA to form intraparticle hybridization, the DNA must bend. Because bending requires extra energy, hairpin formation and intraparticle hybridization therefore requires more energy than interaction between two linear stretches of DNA, such as interparticle hybridization.

The ability of DNA to deform may be measured by its persistence length. Increasing the persistence of the DNA (and the stiffness therefore) makes intraparticle interactions less favorable. Accordingly as shown in FIG. 25, the use of a 60 bp DNA containing a double stranded 50 bp segment has a persistence length of 50 nm, which is longer than the length of the double stranded portion. By contrast, a 60 bp single strand has a persistence length of less than 5 nm.

Temperature is also an important factor in controlling the relative proportion of interparticle versus intraparticle/hairpin formation. The graph at the bottom of FIG. 25 shows an experiment measuring the number of singlet (isolated particles) in a pool of particles with palindromic DNA surfaces. At low temperature, intraparticle/hairpin formation is favored, resulting in less free ends to interact with another particle. As the temperature is raised, the energetically disfavored intraparticle and hairpin hybridizations are reduced, in favor of interparticle hybridization, and therefore resulting in the formation of clusters of particles, as the number of singlets drops. Raising the temperature further, however, results in melting of the particles.

The kinetics of inter- and intraparticle hybridization is also usefully employed, as shown in FIG. 26. In the experiment, aggregates melt at 46 C. If the temperature is rapidly reduced to 14 C in less than 150 s (fast temperature quench), the vast majority of particles remain as singlets. By contrast, a slow (250 s) drop to 31 C (slow temperature quench) results in fewer singlets, and more particles.

Figure 27:
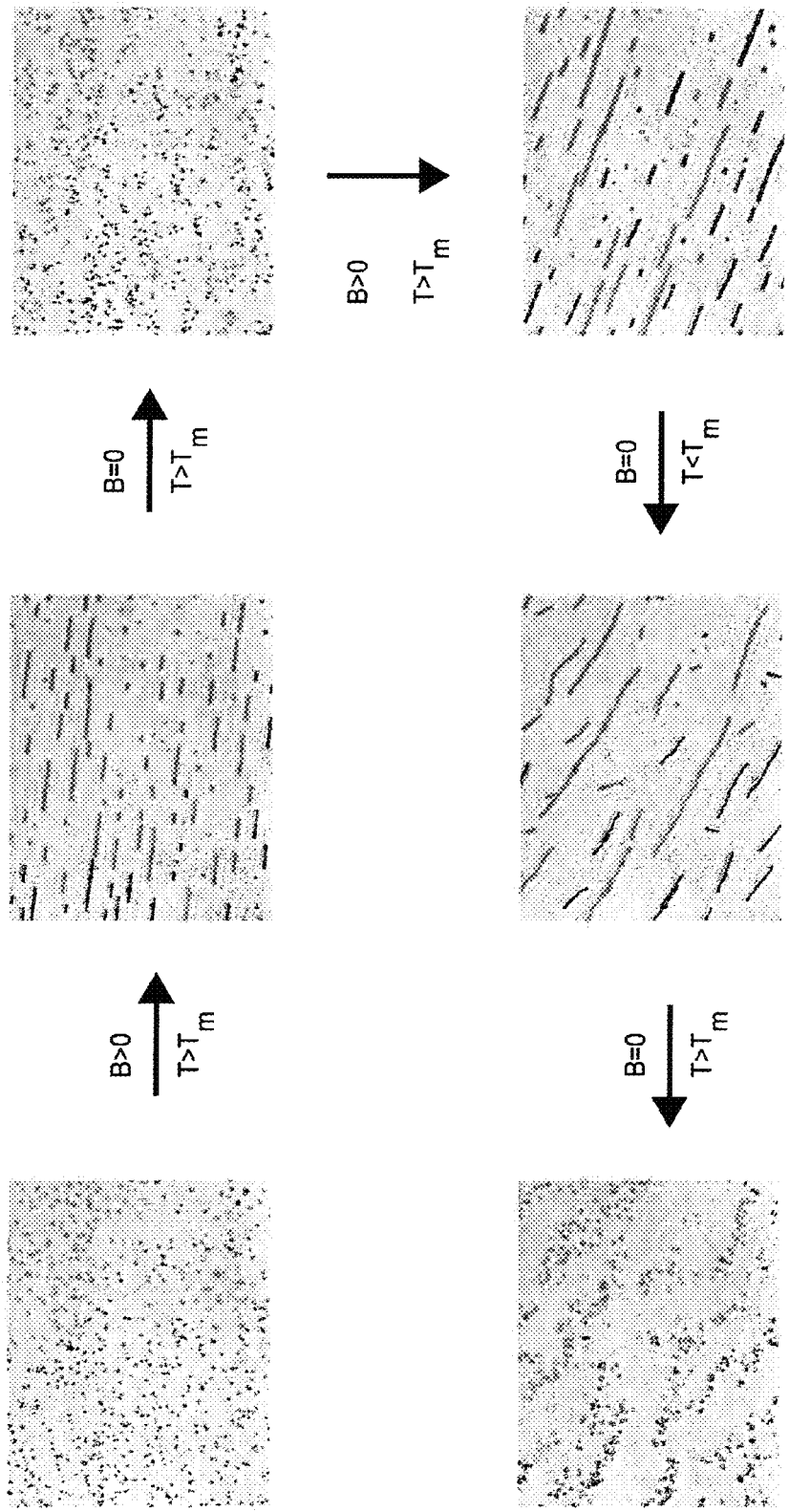
FIG. 27 Magnetic beads with a palindrome, and behaviour in response to variations in magnetic flux density (B), and temperature (T). Tm is the melting/annealing point of the complementary DNA strands.

Beads can be arranged by multiple means. FIG. 27 shows how magnetic beads with a palindromic DNA interact in response to variations in magnetic flux density (B), and temperature (T). $T_m$ is the melting/annealing point of the complementary DNA strands. When B is raised, but above the melting point, the beads form chains along the lines of the magnetic field. If the field is turned off, the chain dissociates. If the field is then reactivated above $T_m$, and then the temperature lowered to below $T_m$, the beads will form a chain that remains when B=0. When T is again raised, the chain dissociates. This experiment demonstrates that the magnetic field can be used to organize the beads, and the temperature is modulated to fix the beads in relationship with each other even in the absence of the magnetic field. This DNA-mediated interaction is fully reversible by changing the temperature.

It was then demonstrated that the DNA-mediated interaction could be made irreversible through the use of psoralen and UV. Beads with the palindrome TACAGCTGTA (SEQ ID NO: 5) aggregate below $T_m$, and the aggregation is reversible by raising the temperature. However, if the beads are allowed to aggregate in the presence of psoralen, and then exposed to UV, subsequent elevation of the temperature will not cause disaggregation, because the DNA between adjacent particles has been crosslinked. By contrast, beads with the palindrome CCAGCTGG formed reversible aggregates below $T_m$, but exposure to psoralen and UV did not result in permanent aggregates, because the palindrome does not contain an AT pair which is necessary for psoralen and UV to cross link the DNA.

In another experiment, a chain of magnetic beads formed under the influence of a magnetic field were then annealed (by lowering the temperature) and crosslinked with psoralen/UV treatment. These particles, bearing a nonpalindromic sequence, specifically interacted with nonmagnetic particles bearing the complement, as shown in FIG. 28, based entirely on DNA interactions. However, there is a problem of particle seed interactions in which the singlet particles prefer to reside in the interstices of the seed, and bind to two adjacent particles. This results in disruption of the correct spacing of the particles in the daughter strand. One solution is to provide at least 3 different beads (flavors) so that there are no favorable interstices. Another solution is to assemble the complementary daughter strand in linear manner, relying on the previous correct positioning of the preceding particle in the daughter strand. Another, related, solution is to have the strand possess elements of directionality, similar to that seen in DNA replication. Patchy particles, which do not possess a uniformly coated surface, can be used to provide directionality to the chain.

Surface functionalization using DNA can be a very useful mechanism for guiding the self-assembly of nano- and micrometer-sized particles. Complementary 'sticky ends' can form specific interparticle links and reproducibly bind at low temperature and unbind at high temperature. The ability of single stranded DNA to form folded secondary structures has not been investigated for controlling (nano) colloidal assembly processes, despite its frequent use in DNA nanotechnology. In this example is illustrated the mechanism to carry out loop and hairpin formation in the DNA coatings of micrometer-sized particles which gives us in situ control over the inter-particle binding strength and association kinetics. This methodology can be finely tuned and even the attractions switched off between particles, rendering them inert unless they are heated or held together in the manner of a nanocontact glue. The kinetic control offered by the switchable self-protected attractions is explained with a simple quantitative model (non-limiting explanation) that emphasizes the competition between intra- and inter-particle hybridization. Practical utility is demonstrated by the assembly of designer clusters in concentrated suspensions. With self-protection, both the suspension and assembly product are stable, whereas conventional attractive colloids would quickly aggregate. This functionality makes our self-protected colloids a unique material that greatly extends the utility of DNA-functionalized systems, enabling more versatile, multi-stage assembly approaches.

Example II

The particle association and structural organization of DNA functionalized systems are equilibrium processes that depend solely on the system temperature, relative to the particles' DNA-dependent dissociation temperature. This is, for instance, demonstrated by our observations on mixtures of beads that form normal Watson-Crick pairs of complementary $C_N/C'_N$ sticky ends (interaction scheme Ia, see FIG. 29). FIG. 30a shows the fraction of non associated particles, or singlet fraction, as a function of time in an experiment where the temperature was decreased from 52 to 20° C. (t<810 s) and then ramped back up (t>810 s). Clearly, as soon as we go below the particles' dissociation temperature ($T_{dis} \approx 40°$ C.), the singlet fraction quickly drops to zero, and the particles come together in extensive structures. Conversely, when we increase the temperature above $T_{dis}$ the aggregates quickly dissociate. The rate of temperature change determines how fast $T_{dis}$ is reached, but it does not change the qualitative shape of the curves.

Figure 29:
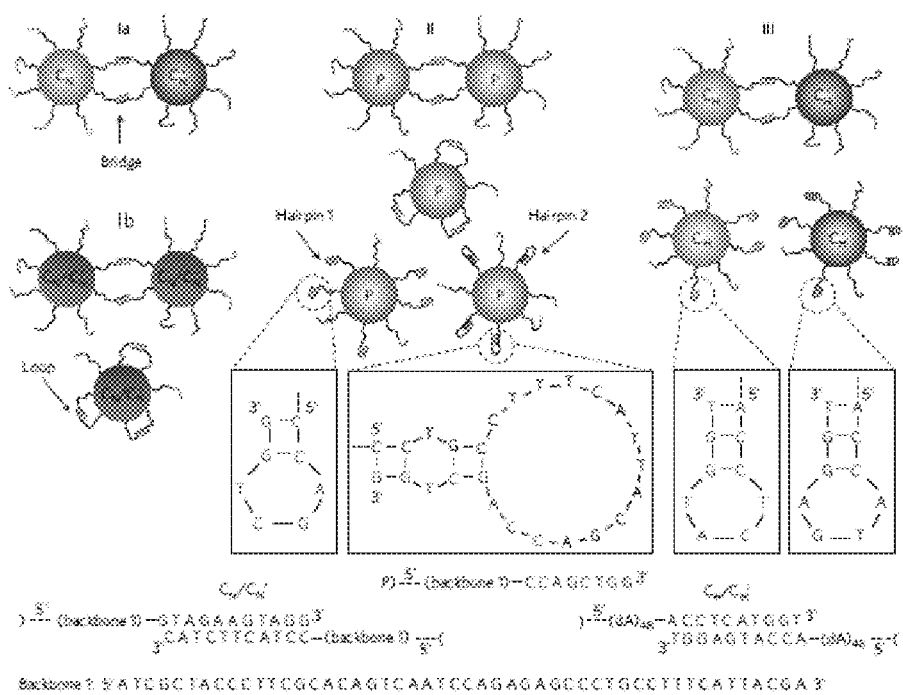
FIG. 29 illustrates schematically conventional and self-protected DNA-mediated interaction schemes including inter- and intra-particle DNA hybridization associated with the different experimental interaction schemes; interaction scheme 1a-1b involves a normal, secondary-structure free pair of complementary sticky ends, either grafted to separate beads (1a) or mixed on the same bead (1b); interaction scheme 11 used a self-complementary, or palindromic, sticky end; besides self-protective loops, this sequence can form two different hairpin structures: hairpin 1 involves only the sticky end sequence, whereas hairpin 2 forms between the sticky end and the backbone (for both $T_m \approx 34°$ C.); interaction scheme 111 consisted of a Watson-Crick pair on separate beads, where each of the sticky ends can form its own protective hairpin ($T_m \approx 43\text{-}45°$ C.). Figure discloses SEQ ID NOS 8-14, respectively, in order of appearance.

Much more flexibility is gained if the sticky ends possess secondary conformations, such as hairpins and loops due to intra-particle complementarity (for example, interaction scheme II, FIG. 29). Such secondary structures form in fractions of a microsecond, as estimated from the rotational diffusion time of single stranded DNA with an end-to-end distance of ~14 nm. This should be compared with the association time of the particles, which depends on their diffusion constant and concentration, and which is of the order of minutes for micrometer-sized beads. As long as the secondary structures have smaller binding energies than the inter-particle bridges, particle association should in principle still be possible. However, in a fast temperature quench, extensive secondary structure formation will occur inside the DNA coatings of the individual beads before they encounter each other. Here, we explore the in situ control that this self-protection mechanism offers over the number of sticky ends available for inter-particle bridging which is one of the main parameters that determine the particles' association strength and kinetics and the new possibilities that this offers for the assembly of designer structures.

FIG. 30b demonstrates that it is indeed the competition between the quench rate and the particles' diffusive encounter rate that matters. Unlike conventional DNA-functionalized particles (see FIG. 30a), a fast temperature quench consistently arrests the aggregation of self-protective scheme II particles at a non-zero singlet fraction, which is higher for smaller particle concentrations (in FIG. 30b is shown a series of horizontal plateaux). The occurrence of aggregation followed by inactivation indicates that at the start of the quench inter-particle bridges dominate, whereas at lower temperatures intra-particle loop and hairpin formation reduce the number of unprotected sticky ends, to the point that it arrests the aggregation. At lower particle concentrations, fewer associative collisions occur before the interactions are completely inhibited, giving a higher plateau. The difference in the melting temperatures of the loops and inter-particle bridges, the former being lower than the latter, is due to the different configurational entropy costs associated with these two hybridization geometries. Apparently, the particles' diffusive encounters, estimated to last ~0.2 ms, are too short for the low-temperature loops and hairpins to open up and to form more stable inter-particle bridges. From FIG. 30b, it can also be seen that when the temperature is increased again (t>400 s), dehybridization of the loops and hairpins reactivates the particle association, leading to a dip in the singlet fraction before the beads enter the familiar dissociation transition.

In addition to the quench rate/concentration dependence, FIGS. 31a and 31b highlight two other important properties of our self-protected colloids. First, FIG. 31a shows the pronounced temperature dependence of the association kinetics in an experiment where we monitored the diffusive aggregation of scheme II beads at several different temperatures. From the inset, it is clear that the temperature response of these self-protective beads is much stronger than that of conventional scheme Ia beads. This results from the fact that the sticking probability of the self-protective beads depends on the fraction of unprotected sticky ends, which changes exponentially with the temperature, $f_u \alpha \exp(\Delta G_{DNA}/k_B T)$ (here, $\Delta G_{DNA}$ represents the hybridization free energy of the protective secondary structures). For conventional beads, all sticky ends are always unprotected, making their association kinetics only weakly temperature dependent. Second in FIG. 31b, we determined the fraction of scheme II particles that remained bound, after keeping them close together in chain-like structures, induced by a weak magnetic field. The inset shows that the association kinetics again speed up with the temperature, but that the timescales are three orders of magnitude shorter than the ones associated with diffusive aggregation. This is because by keeping the particles in each other's proximity, the field allows for multiple binding attempts without slow, long-distance particle diffusion in between.

Taking advantage of the special properties of our self-protected colloids, we can overcome some of the main limitations of conventional DNA-functionalized systems. As an example, we demonstrate the directed assembly of ring-like structures, using interaction scheme II and holographic optical traps (FIGS. 32a to 32d). We either shrink a circular array of point-like traps until the particles are in close proximity (stationary trapping) or we use a continuous, rotating ring trap in which the particles can freely move around (dynamic trapping). At high temperature, but well below the particles' dissociation transition, the self-protection is limited and the suspension behaves like a conventional DNA-functionalized system. This means that any positioning mistakes that occur while the particles are being arranged into the desired structure (the pre-assembly stage) immediately cause particles to stick in the wrong place. For instance, accidentally trapping two particles in the same stationary trap creates doublets (FIG. 32a), whereas dynamic trapping yields only disordered clusters (FIG. 32a). In contrast, at low temperature the sticky ends are well protected, providing ample time to correct any positioning mistakes in the pre-assembly stage (FIG. 32b).

The particles inside the structures spontaneously bind together or can be triggered to do so by a brief elevation of the temperature. It follows from FIG. 31 that the temperature can be chosen such that the structures crosslink in ~5-10 min, and the diffusive aggregation is negligible for many hours. Thus, whereas at high temperatures the newly assembled structures soon aggregate and become decorated with other particles (FIGS. 32c and 32e), at low temperatures the structures and surrounding suspension are nearly inert (FIGS. 32d and 32f). These experiments also demonstrate that we can deliberately switch the association on and off without dissociating the previously assembled structures. Clearly, our self-protected particles greatly facilitate the fabrication of designer structures that are inert to further association, without the need to work under dilute conditions. Moreover, it enables multi-stage assembly approaches in which previously formed structures can for instance be isolated, transferred to a new particle suspension and kept stable for a prolonged time (FIG. 32h). These properties stand in sharp contrast to those of conventional DNA-functionalized systems that can switch only between fully associated and fully dissociated states. As is demonstrated by FIGS. 32g and 32i, the latter means that any newly assembled structure of conventional DNA-functionalized particles will be subject to rapid and uncontrollable aggregation, which compromises their practical use.

A quantitative understanding of the self-protection can be obtained by modelling a series of association-dissociation curves that were obtained at different quench rates (FIG. 33a). Here, we outline the main principles; more details will be presented elsewhere. In its simplest form, we treat the particle association and dissociation as a reaction that interconverts singlets (S, concentration $c_1$) and doublets (S2, concentration $c_2$):

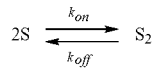

This reaction is governed by the rate equations:

$$\frac{dc_1}{dt} = -2k_{on}c_1^2 + 2k_{off}c_2$$

$$\frac{dc_2}{dt} = -k_{on}c_1^2 - k_{off}c_2$$

Figure 33C:
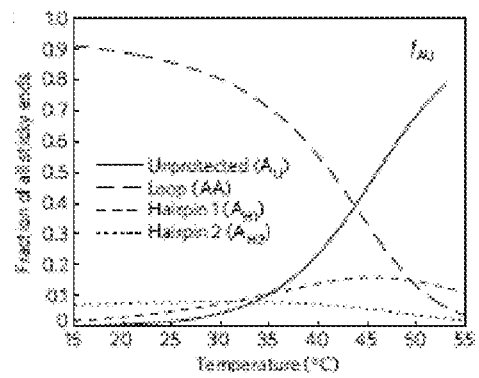

In the experiments of FIG. 33a, each time t corresponds to a particular temperature, T(t). The association rate parameter, $k_{on}$, depends on the diffusive flux of singlets, in two dimensions $k_{diff}=2k_BT(t)/3\eta R_p$ ($k_B$ is the Boltzmann constant, $\eta$ is the viscosity and $R_p$ is the particle radius), and the dissociation rate parameter follows from the free energy for bead-bead hybridization, $k_{off}(t)\alpha \exp(\Delta F_{bead}/k_BT)$. The horizontal plateaux in the experimental aggregation curves indicate that the conversion of loops and hairpins into inter-particle bridges occurs on a timescale that is significantly longer than the duration of a diffusive particle encounter. Moreover, by the time two particles encounter each other, a hybridization equilibrium will have been established inside their DNA coatings. Therefore, we assume that in the early stages of association, $\Delta F_{bead}$ is determined by the fraction of unprotected sticky ends at the moment of collision, which follows from the partition function of all of the different hybridization possibilities on an isolated particle, Supplementary Equations S1-S3 and schematic diagram 1, (see FIG. 33b). Using the predicted solution hybridization free energies, $\Delta G^0$ (see the Methods section), and including an appropriate configurational entropy cost, $\Delta S_{conf}$, for the loops ($\Delta G_{loop} = \Delta G_p^0$, solution $-T\Delta S_{conf,loop}$), we find the bond distributions in FIG. 33c. Taking the fraction of unprotected sticky ends, $f_{AU}$, we obtain $\Delta F_{bead}$ from the expression that has been previously published for two surfaces that interact with a certain fixed number of active sticky ends:

$$\frac{\Delta F_{bead}}{k_BT} = -\ln\left(\left[1 + f_{AU}m\exp\left(-\frac{\Delta G_{bridge}}{k_BT}\right)\right]^{f_{AU}N_b} - 1\right)$$

Figure 33D:
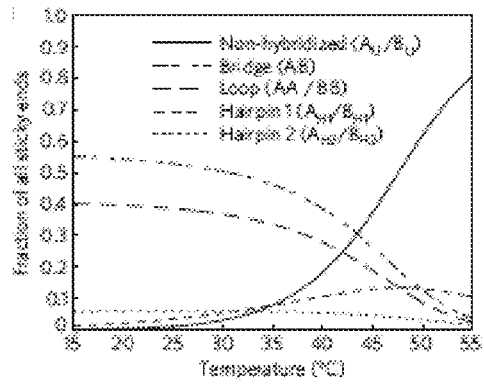

Here, $N_b$ is the maximum number of bridges that can form if all sticky ends are unprotected, m is the number of opposing sticky ends within reach and ($\Delta G_{bridge} = \Delta G_p^0$, solution $-T\Delta S_{conf,bridge}$). To model the particles' high-temperature dissociation transition (t>>810 s in FIG. 33a) we follow a similar approach, but now we consider the equilibrium that includes intra- and inter-particle hybridization simultaneously, because the particles inside the aggregates are in prolonged contact, enabling the interconversion of loops, hairpins and inter-particle bridges. The total partition function and $\Delta F_{bead}$ are then applied (see FIG. 33b), and FIG. 33d shows the bond distributions. Finally, we fit the experimental data by numerically solving for the evolution of the rate equations (equation (1)), using the experimental singlet concentration at t=0 and temperature profiles, T(t), as input. Keeping all other parameters fixed at their known or estimated values, we obtained the fits in FIG. 33a with the configurational entropy costs $\Delta S_{conf,bridge}=12.6\ k_B$ and $\Delta S_{conf,bridge}=13.5\pm0.2\ k_B$. We have previously shown that these values agree fairly well with those obtained from simple geometrical estimates. Moreover, the computed curves show the expected strong dependence on the quench rate.

Figure 33E:
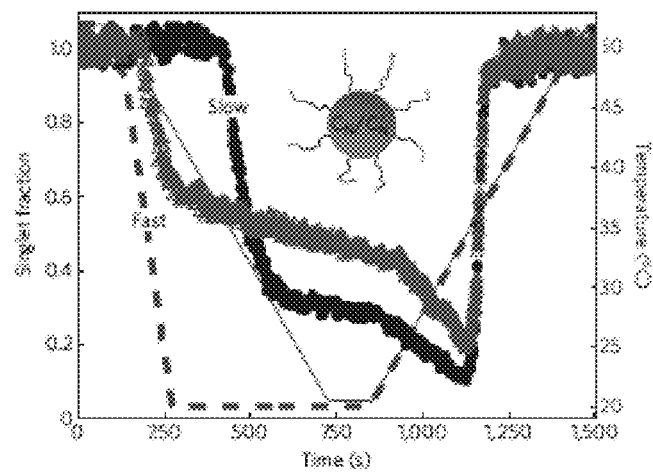

FIG. 33c indicates that for interaction scheme II the main contribution to the self-protection comes from loop formation. We verified this with a system in which the normal $C_N$ and $C'_N$ sticky ends were mixed in a 50=50 ratio on the same bead, giving loop formation, but no hairpins (interaction scheme Ib, FIG. 29). FIG. 33e shows that in broad lines the association-dissociation behaviour for this system is indeed similar to that of scheme II. However, the $C_N/C'_N$ system suffers from a 'pairing' problem, in that a certain fraction of sticky ends fails to find a nearby partner for loop formation. This prevents a complete arrest of the aggregation, hence the tilt of the plateaux in FIG. 33e. Apparently, the seemingly insignificant hairpin formation of scheme II has an important role in circumventing the pairing problem, as the mono-molecular hairpins protect sticky ends that remain without a binding partner. We also point out that similar switchable self protected interactions can be established with sticky ends that formonly hairpins and that have no intra-particle complementarity, such as, for instance, the $C_H/C'_H$ pair of interaction scheme III (FIG. 29).

In summary, we have added secondary structure formation to the DNA toolkit that facilitates the (self-)assembly of nano- and micrometer-sized particles, and we have developed a non-limiting example model that provides a quantitative understanding of the particle association. Besides facilitating the fabrication of designer structures, the self protected interactions will impart selective, self-healing and self reinforcing properties to the particle assemblies. Selective, because particles only connect if held sufficiently long in the right position; here done with optical or magnetic traps, but other methods, such as templating, are conceivable as well. Self-healing, because the material can be broken into smaller, stable pieces that nevertheless have the ability to reconnect. Self-reinforcing, because the initially weak bridging may be followed by the formation of more bonds through the opening of intra-particle loops and hairpins, either spontaneously or triggered by heat. The last property is reminiscent of certain forms of cell adhesion, where rapid capture is followed by slow consolidation, and, together with the other functionalities, this will enable more complex assembly schemes.

Several methods of DNA and particle preparation are now described herein. All of our DNA constructs consisted of a highly flexible, single-stranded backbone of 50 nucleotides long with a short, 8-11 nucleotides long single-stranded sequence at its 3' terminus. The $C_N/C'_N$ and P oligonucleotides were purchased from Integrated DNA Technologies USA, whereas we synthesized the $C_H/C'_H$ sequences ourselves, on an Applied Biosystems 394 DNA synthesizer. After completion, we removed the oligonucleotides from the support and deprotected them using conventional phosphoramidite procedures. The backbone of the DNA constructs was attached to a 50 biotin group through a short, flexible polyethyleneglycol spacer. For most experiments, we functionalized 1:05 μm diameter, streptavidin-coated, paramagnetic polystyrene Dynabeads (MyOne Streptavidin C1, Molecular Probes) with the biotinylated DNA constructs, by incubating 5 μl bead suspension for 30 min at 55° C. with 5 μl of 6 μl 41 oligonucleotide solution and 65 μl suspension buffer (10 mM phosphate/50 mM NaCl and 0.5% w/w Pluronic surfactant F127, pH 7.5). Strong sedimentation of these high-density particles quickly led to essentially two-dimensional microscopy samples. For the optical trapping experiments, we used 1:0-μm-diameter, non-fluorescent, neutravidin-labelled polystyrene Fluospheres (Invitrogen), combining 5 μl bead suspension with 10 µl oligonucleotide solution and 85 µl suspension buffer. These particles had a density close to that of water and remained suspended throughout the entire sample for many hours. In all cases, we removed excess and non-specifically adsorbed DNA by centrifuging and resuspending the particles three times in 100 µl suspension buffer; we repeated this washing procedure twice, heating in between for 30 min at 55° C.

Regarding the thermodynamic parameters of the oligonucleotides, we obtained the enthalpic and entropic contributions to the hybridization free energies ($\Delta G^0 = \Delta H^0 - T\Delta S^0$) of the sticky ends and their secondary structures from the Mfold webserver, using [Na$^+$]=68 mM for the suspension buffer. $C_N/C'_N$: $\Delta H^0$=370 kJ mol$^{-1}$, $\Delta S^0$=1.08 kJ mol$^{-1}$ K$^{-1}$; P: $\Delta H^0$=−296 kJ mol$^{-1}$, $\Delta S^0$=841 J mol$^{-1}$ K$^{-1}$; P hairpin 1: $\Delta H^0$=84.9 kJ mol$^{-1}$, $\Delta S^0$=−267 J mol$^{-1}$ K$^{-1}$; P hairpin 2: $\Delta H^0$=−148 kJ mol$^{-1}$, $\Delta S^0$=−472 J mol$^{-1}$ K$^{-1}$; $C_H/C'_H$: $\Delta H^0$=−285 kJ mol$^{-1}$, $\Delta S^0$=−798 J mol$^{-1}$ K$^{-1}$; $C_H$ hairpin: $\Delta H^0$=−81.6 kJ mol$^{-1}$, $\Delta S^0$=−258 J mol$^{-1}$ K$^{-1}$; $C'_H$ hairpin: $\Delta H^0$=−71.1 kJ mol$^{-1}$, $\Delta S^0$=−223 J mol$^{-1}$ K$^{-1}$.

DNA-functionalized particle suspensions are confined to a borosilicate glass capillary (inner dimensions 2:0×0:1 mm, Vitrocom), which was previously cleaned by oxygen plasma etching and hydrophobized by silanization. The capillary was then mounted on a special stage set-up on a Leica DMRXA light microscope, which enabled fine temperature control, while imaging in a conventional transmission mode. To study the association kinetics in the presence of a magnetic field, we centred the iron cores of an electromagnet coil (made in-house) around the microscope objective.

Temperature-regulated holographic optical trapping set-up. For optical trapping, 10 µl of DNA-functionalized particle suspension was sealed between two 18×18 mm$^2$, number 1 cover slips, which were previously cleaned by oxygen plasma etching and hydrophobized by silanization. The sample then was mounted on a sapphire microscope slide and centred on a 14.5-mm-diameter hole passing through a water-cooled Peltier element (Melcor, series SH 1.0-95-06). This enabled us to control the sample's temperature while simultaneously providing optical access for transmission-mode imaging and optical micromanipulation. Holographic optical traps were powered by a frequency-doubled diode-pumped solid-state laser (Coherent Verdi), operating at a wavelength of 532 nm. A reflective liquid crystal spatial light modulator (Hamamatsu X8267-16 PPM) imprinted the beam's wavefronts with computer-generated holograms encoded with the desired trapping pattern. This laser profile was then directed into the input pupil of a ×100, numerical aperture: 1.4, Plan Apo oil-immersion objective mounted on a Nikon TE-2000U inverted optical microscope, and was focused into optical traps.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention.

We claim:

1. A replicable artificial composition comprising,
   at least two particles, A' and B', having an A'-B' bond therebetween comprising a double-stranded DNA having an adenine-thymine/thymine-adenine pairing, further comprising a surface-exposed first single-stranded nucleic acid on particle A' and a surface-exposed second single-stranded nucleic acid on particle B'; and
   at least two particles, A and B, having an A-B bond therebetween comprising a double-stranded DNA having an adenine-thymine/thymine-adenine pairing, further comprising a surface-exposed third single-stranded nucleic acid on particle A and a surface-exposed fourth single-stranded nucleic acid on particle B,
   the first single-stranded nucleic acid on particle A' specifically and reversibly interacting with the surface-exposed third single-stranded nucleic acid on particle A and the second single-stranded nucleic acid on particle B' specifically and reversibly interacting with the surface-exposed fourth single-stranded nucleic acid on particle B;

wherein the A'-B' bond and the A-B bond are irreversible under conditions in which interactions of the third single-stranded nucleic acid of particle A and the first single-stranded nucleic acid of particle A' and interactions of the fourth single-stranded nucleic acid of particle B and the second single-stranded nucleic acid of particle B' are reversible;

further wherein the first single-stranded nucleic acid and the third single stranded nucleic acid do not hybridize through adenine-thymine/thymine-adenine pairings and the second single-stranded nucleic acid and the fourth single-stranded nucleic acid do not hybridize through adenine-thymine/thymine-adenine pairing and the irreversible conditions comprise psoralen mediated crosslinking.

2. The composition of claim 1, wherein said particles are colloidal particles.

3. The composition of claim 2, wherein said colloidal particles are patchy particles.

4. The composition of claim 1, wherein said first, second, third, and fourth chemical moieties comprise DNA.

5. The composition of claim 4 in which each of the first, second, third, and fourth single-stranded DNA comprise a sequence and its complement selected from the group consisting of:

i.   AGCTGTCAAGGA;    (SEQ ID NO: 3)
         and
    ii.  GCCTCTGAGAGA.    (SEQ ID NO: 4).

6. A replicable artificial composition comprising:
a first particle A' having a first A' chemical moiety and a second A' chemical moiety;
a second particle B' having a first B' chemical moiety and a second B' chemical moiety;
a third particle A having a first A chemical moiety and a second A chemical moiety;
a fourth particle B having a first B chemical moiety and a second B chemical moiety;
the first A' chemical moiety irreversibly interactable with the first B' chemical moiety and the first A chemical moiety irreversibly interactable with the first B chemical moiety
wherein each of the first A' chemical moiety, the first B' chemical moiety, the first A chemical moiety, and the first B chemical moiety are DNA having an adenine-thymine/thymine-adenine pairing able to undergo psoralen-mediated crosslinking; and
the second A' chemical moiety reversibly interactable with the second A chemical moiety and the second B' chemical moiety reversibly interactable with the second B chemical moiety wherein each of the second A' chemical moiety, the second B' chemical moiety, the second A chemical moiety, and the second B chemical moiety are DNA lacking adenine-thymine/thymine-adenine pairing.

7. The replicable artificial composition of claim 6, wherein the transverse moieties are palindromic DNA sequences.

8. The replicable artificial composition of claim 6, wherein at least one of the first particle, the second particle, the third particle, and the fourth particle include a polymeric brush configured to reduce nonspecific interactions between particles.

9. The replicable artificial composition of claim 6, wherein the first particle and the second particle are magnetic.

10. The composition of claim 4 in which the A'-B' and the A-B bond each comprise a sequence selected from a sequence and its complement, selected from the group consisting of:

i.   CCATGCGCATGG;    (SEQ ID NO: 1)
         and
    ii.  AGCATGCATGCT     (SEQ ID NO: 2).

* * * * *

SEQUENCE LISTING

```
<160> NUMBER OF SEQ ID NOS: 14

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccatgcgcat gg                                                         12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agcatgcatg ct                                                         12

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 3
agctgtcaag ga                                                              12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcctctgaga ga                                                              12

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tacagctgta                                                                 10

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tcgacagttc ca                                                              12

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcgacagttc ct                                                              12

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cctgcctttc attacgacca gctgg                                                25

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
```

```
acctcatggt                                                          10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
accatgaggt                                                          10

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtagaagtag g                                                        11

<210> SEQ ID NO 12
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaaaaaaaa aaaaaaaaaa aaaaaaaaaa aaaaaaaaaa aaaaaaaaac ctcatggt    58

<210> SEQ ID NO 13
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaaaaaaaaa aaaaaaaaaa aaaaaaaaaa aaaaaaaaaa aaaaaaaaac catgaggt    58

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atcgctaccc ttcgcacagt caatccagag agccctgcct ttcattacga             50
```